US011179312B2

(12) United States Patent
Sun et al.

(10) Patent No.: US 11,179,312 B2
(45) Date of Patent: Nov. 23, 2021

(54) AQUEOUS COMPOSITIONS FOR THE TREATMENT OF HAIR

(71) Applicant: Momentive Performance Materials Inc., Waterford, NY (US)

(72) Inventors: Kunshan Sun, Millwood, NY (US); Anne Dussaud, Tarrytown, NY (US); Karl-Heinz Stachulla, Leverkusen (DE); Christian Wenske, Solingen (DE); Katharina Streicher, Leverkusen (DE); Roland Wagner, Bonn (DE)

(73) Assignee: Momentive Performance Materials Inc., Waterford, NY (US)

( * ) Notice: Subject to any disclaimer, the term of this patent is extended or adjusted under 35 U.S.C. 154(b) by 11 days.

(21) Appl. No.: 15/613,988

(22) Filed: Jun. 5, 2017

(65) Prior Publication Data
US 2018/0344619 A1 Dec. 6, 2018

(51) Int. Cl.
| | |
|---|---|
| A61K 8/89 | (2006.01) |
| A61K 8/36 | (2006.01) |
| A61Q 5/06 | (2006.01) |
| A61Q 5/02 | (2006.01) |
| A61K 8/06 | (2006.01) |
| A61K 8/58 | (2006.01) |
| A61Q 5/12 | (2006.01) |
| A61Q 5/08 | (2006.01) |
| A61Q 5/10 | (2006.01) |
| A61K 8/39 | (2006.01) |
| A61Q 5/00 | (2006.01) |
| C08L 83/08 | (2006.01) |
| C08L 83/06 | (2006.01) |
| C08G 77/14 | (2006.01) |
| C08G 77/26 | (2006.01) |
| C08G 77/20 | (2006.01) |

(52) U.S. Cl.
CPC ................ *A61K 8/89* (2013.01); *A61K 8/062* (2013.01); *A61K 8/39* (2013.01); *A61K 8/585* (2013.01); *A61Q 5/004* (2013.01); *A61Q 5/06* (2013.01); *A61Q 5/065* (2013.01); *A61Q 5/08* (2013.01); *A61Q 5/10* (2013.01); *A61Q 5/12* (2013.01); *C08L 83/06* (2013.01); *C08L 83/08* (2013.01); *A61K 2800/94* (2013.01); *A61Q 5/02* (2013.01); *C08G 77/14* (2013.01); *C08G 77/20* (2013.01); *C08G 77/26* (2013.01)

(58) Field of Classification Search
None
See application file for complete search history.

(56) References Cited

U.S. PATENT DOCUMENTS

| | | |
|---|---|---|
| 1,927,339 A | 9/1933 | Ernster |
| 3,558,741 A | 1/1971 | Holub et al. |
| 4,075,167 A | 2/1978 | Takamizawa et al. |
| 4,698,178 A | 10/1987 | Hüttinger et al. |
| 4,833,225 A | 5/1989 | Schaefer et al. |
| 4,891,166 A | 1/1990 | Schaefer et al. |
| 4,931,062 A | 6/1990 | Bay et al. |
| 4,981,485 A | 1/1991 | Motono |
| 5,098,979 A | 3/1992 | O'Lenick, Jr. |
| 5,151,473 A | 9/1992 | Herzig |
| 5,153,294 A | 10/1992 | O'Lenick, Jr. |
| 5,166,297 A | 11/1992 | O'Lenick, Jr. |
| 5,433,753 A | 7/1995 | Dahmen et al. |
| 5,489,429 A | 2/1996 | Griat et al. |
| 5,686,011 A | 11/1997 | Lohmann et al. |
| 5,711,942 A | 1/1998 | Eicken et al. |
| 5,854,319 A | 12/1998 | O'Lenick, Jr. et al. |
| 6,110,230 A | 8/2000 | Friedrich et al. |
| 6,143,286 A * | 11/2000 | Bhambhani ............ A61K 8/416 424/407 |
| 6,240,929 B1 | 6/2001 | Richard et al. |
| 6,277,445 B1 | 8/2001 | Hasegawa et al. |
| 6,379,751 B1 | 4/2002 | Schafer et al. |
| 6,544,499 B1 | 4/2003 | Glenn, Jr. et al. |
| 6,555,505 B1 | 4/2003 | King et al. |
| 6,630,136 B1 * | 10/2003 | Dubief .................. A61K 8/731 424/70.11 |
| 6,664,342 B1 | 12/2003 | Köhler et al. |
| 6,730,766 B2 | 5/2004 | Schattenmann et al. |
| 6,753,369 B2 | 6/2004 | Hill, Jr. et al. |
| 7,041,767 B2 | 5/2006 | Lange et al. |
| 7,148,327 B2 | 12/2006 | Kelly et al. |
| 7,217,777 B2 | 5/2007 | Lange et al. |
| 7,329,707 B2 | 2/2008 | Sandner et al. |
| 7,563,856 B2 | 7/2009 | Lange et al. |
| 7,563,857 B2 | 7/2009 | Lange et al. |
| 9,144,537 B1 | 9/2015 | Pressly et al. |

(Continued)

FOREIGN PATENT DOCUMENTS

| | | |
|---|---|---|
| CA | 2092440 A1 | 3/1992 |
| CA | 2219541 A1 | 5/1998 |

(Continued)

OTHER PUBLICATIONS

Machine translation of JP-56018572-B, original document published Apr. 1981 (Year: 1981).*

(Continued)

*Primary Examiner* — Nissa M Westerberg

(74) *Attorney, Agent, or Firm* — Joseph S. Ostroff

(57) ABSTRACT

The invention relates to aqueous compositions for hair treatment, comprising polyorganosiloxanes A) or organic compounds B) having certain functional groups, in particular aldehyde and unsaturated dicarboxylic acid moieties, hair treatment or hair care compositions comprising the aqueous compositions, a process for the treatment of hair which comprises the steps of providing the aqueous compositions and applying said aqueous compositions to the hair, and the use of the aqueous compositions for the treatment of hair.

27 Claims, 1 Drawing Sheet

(56) References Cited

U.S. PATENT DOCUMENTS

| | | | |
|---|---|---|---|
| 9,308,668 B2 | 4/2016 | Delis et al. | |
| 10,617,617 B1 | 4/2020 | Sun et al. | |
| 2001/0006654 A1* | 7/2001 | Cannell | A61K 8/442 424/400 |
| 2005/0148702 A1* | 7/2005 | Eigen | D06M 13/02 524/100 |
| 2005/0255073 A1 | 11/2005 | Sockel et al. | |
| 2006/0188456 A1 | 8/2006 | Ferenz et al. | |
| 2007/0048235 A1 | 3/2007 | Harmalker et al. | |
| 2007/0106045 A1 | 5/2007 | Lange et al. | |
| 2007/0129520 A1 | 6/2007 | Ochs et al. | |
| 2007/0287987 A1 | 12/2007 | Katsarava et al. | |
| 2008/0027202 A1 | 1/2008 | Ferenz et al. | |
| 2008/0161500 A1 | 7/2008 | Stark et al. | |
| 2008/0213208 A1 | 9/2008 | Moeller et al. | |
| 2009/0000638 A1 | 1/2009 | Wood et al. | |
| 2009/0062459 A1 | 3/2009 | Thum et al. | |
| 2009/0076238 A1 | 3/2009 | Lange et al. | |
| 2009/0137764 A1 | 5/2009 | Sutton et al. | |
| 2009/0165812 A1 | 7/2009 | Resnick et al. | |
| 2009/0211593 A1 | 8/2009 | Coppola et al. | |
| 2010/0266651 A1 | 10/2010 | Czech et al. | |
| 2011/0021955 A1 | 1/2011 | Byblow et al. | |
| 2011/0039948 A1 | 2/2011 | Lange et al. | |
| 2011/0219552 A1 | 9/2011 | Zhou et al. | |
| 2012/0031420 A1 | 2/2012 | Gormley et al. | |
| 2012/0289649 A1 | 11/2012 | Wagner et al. | |
| 2013/0259820 A1 | 10/2013 | Snyder et al. | |
| 2014/0308224 A1 | 10/2014 | Pilz et al. | |
| 2015/0011449 A1 | 1/2015 | Snyder et al. | |
| 2015/0037270 A1* | 2/2015 | Pressly | A61Q 5/02 424/70.1 |
| 2015/0231069 A1* | 8/2015 | Modi | A61K 9/1075 424/455 |
| 2015/0305469 A1 | 10/2015 | Paul | |
| 2015/0328102 A1 | 11/2015 | Pressly | |
| 2016/0016397 A1 | 1/2016 | Xie et al. | |
| 2016/0175220 A1* | 6/2016 | Washington | A45D 7/06 132/206 |
| 2017/0291994 A1 | 10/2017 | Wagner et al. | |
| 2018/0344619 A1 | 12/2018 | Sun et al. | |
| 2020/0170923 A1 | 6/2020 | Sun et al. | |

FOREIGN PATENT DOCUMENTS

| | | | |
|---|---|---|---|
| CN | 104069033 A | 10/2014 | |
| CN | 104892976 A | 9/2015 | |
| CN | 105062040 A | 11/2015 | |
| CN | 105815536 A | 8/2016 | |
| CN | 106490571 A | 3/2017 | |
| DE | 1099169 B | 2/1961 | |
| DE | 2904164 A1 | 8/1980 | |
| DE | 255346 A1 | 3/1988 | |
| DE | 3800629 A1 | 7/1989 | |
| DE | 4030160 A1 | 3/1992 | |
| DE | 4139090 A1 | 6/1993 | |
| DE | 4318539 A1 | 12/1994 | |
| DE | 19609960 A1 | 9/1997 | |
| DE | 19707970 A1 | 9/1998 | |
| DE | 19859722 A1 | 6/2000 | |
| DE | 19860239 A1 | 7/2000 | |
| DE | 10036553 A1 | 9/2001 | |
| DE | 10036522 A1 | 2/2002 | |
| DE | 10036532 A1 | 2/2002 | |
| DE | 10036533 A1 | 2/2002 | |
| DE | 10253152 A1 | 6/2004 | |
| DE | 102004002208 A1 | 8/2005 | |
| EP | 0650717 A1 | 5/1955 | |
| EP | 0095676 A2 | 7/1983 | |
| EP | 0282720 A2 | 9/1988 | |
| EP | 0282720 B1 | 9/1988 | |
| EP | 0431609 A2 | 6/1991 | |
| EP | 0638128 A1 | 2/1995 | |
| EP | 0780117 A1 | 6/1997 | |
| EP | 0842656 A2 | 5/1998 | |
| EP | 0938590 A1 | 9/1999 | |
| EP | 1108765 A2 | 6/2001 | |
| EP | 1892274 A2 | 2/2008 | |
| EP | 2363387 A2 | 9/2011 | |
| EP | 2576660 B1 | 4/2014 | |
| FR | 2986704 A1 | 8/2013 | |
| GB | 313892 | 6/1929 | |
| GB | 320041 | 9/1929 | |
| GB | 358491 | 10/1931 | |
| GB | 338367 | 2/1933 | |
| GB | 429915 | 6/1935 | |
| GB | 474630 | 11/1937 | |
| GB | 479905 | 2/1938 | |
| GB | 497846 | 12/1938 | |
| GB | 498818 | 1/1939 | |
| GB | 541047 | 11/1941 | |
| GB | 577998 | 6/1946 | |
| GB | 635708 | 4/1950 | |
| GB | 643025 | 9/1950 | |
| GB | 755321 | 8/1956 | |
| GB | 766273 | 1/1957 | |
| GB | 881714 | 11/1961 | |
| GB | 924050 | 4/1963 | |
| GB | 954086 | 4/1964 | |
| GB | 981850 | 1/1965 | |
| GB | 1087783 | 10/1967 | |
| GB | 1427057 | 3/1976 | |
| JP | 50135237 A | 4/1974 | |
| JP | S50135237 A | 10/1975 | |
| JP | S5228948 A | 3/1977 | |
| JP | 56018572 B * | 4/1981 | |
| JP | S57154101 A | 9/1982 | |
| JP | H04353600 A | 12/1992 | |
| JP | H07170904 A | 7/1995 | |
| JP | H09227479 A | 2/1997 | |
| JP | 2001114647 A | 4/2001 | |
| JP | 2004269459 A | 9/2001 | |
| JP | 2002-114849 A | 4/2002 | |
| JP | 2002114849 | 4/2002 | |
| JP | 2002114849 A * | 4/2002 | |
| JP | 2004210724 A | 7/2004 | |
| JP | 2006075137 A | 3/2006 | |
| JP | 2006-169323 A | 6/2006 | |
| JP | 2006169323 | 6/2006 | |
| JP | 2008011739 A | 1/2008 | |
| JP | 2009273441 A | 11/2009 | |
| JP | 2013051916 A | 3/2013 | |
| JP | WO2014077385 A1 | 1/2017 | |
| JP | 2017063619 A | 4/2017 | |
| JP | 2017176006 A | 10/2017 | |
| JP | 2018076278 A | 5/2018 | |
| KR | 20040054557 A | 6/2004 | |
| SU | 187917 | 3/1965 | |
| TW | 201143630 | 12/2011 | |
| WO | 9218457 A1 | 10/1992 | |
| WO | 9301791 A1 | 2/1993 | |
| WO | 9410971 A1 | 5/1994 | |
| WO | 9516664 A1 | 6/1995 | |
| WO | 97/02844 A1 | 1/1997 | |
| WO | 0196444 A1 | 12/2001 | |
| WO | 0210256 A1 | 2/2002 | |
| WO | 0210257 A1 | 2/2002 | |
| WO | 0210259 A1 | 2/2002 | |
| WO | 0210257 A1 | 7/2002 | |
| WO | 03044233 A1 | 5/2003 | |
| WO | 2004069137 A2 | 8/2004 | |
| WO | 2007/061793 A2 | 5/2007 | |
| WO | 2009042083 A2 | 4/2009 | |
| WO | 2010017651 A1 | 2/2010 | |
| WO | 2012027369 A2 | 3/2012 | |
| WO | 2012027389 A2 | 3/2012 | |
| WO | 2012038334 A1 | 3/2012 | |
| WO | 2012084826 A1 | 5/2012 | |
| WO | 2012143371 A1 | 10/2012 | |
| WO | 2013017260 A1 | 2/2013 | |
| WO | 2013117770 A2 | 8/2013 | |
| WO | 2013117771 A2 | 8/2013 | |
| WO | WO-2013117770 A2 * | 8/2013 | ............ A61Q 5/002 |

(56) References Cited

FOREIGN PATENT DOCUMENTS

| WO | 2013148629 A1 | 10/2013 | |
|---|---|---|---|
| WO | 2013148635 A1 | 10/2013 | |
| WO | 2013148935 A1 | 10/2013 | |
| WO | 2014072490 A1 | 5/2014 | |
| WO | 2014072645 A1 | 5/2014 | |
| WO | 2014077385 A1 | 5/2014 | |
| WO | WO-2014072490 A1 * | 5/2014 | ............... A61K 8/24 |
| WO | 2016046178 A1 | 3/2016 | |
| WO | 2016/087795 A1 | 6/2016 | |
| WO | 2017071663 A1 | 5/2017 | |
| WO | 2017/155875 A1 | 9/2017 | |

OTHER PUBLICATIONS

CAPlus abstract for JP-56018572-B, original document published Apr. 1981 (Year: 1981).*

Machine translation of JP-20021114849, original document published Apr. 2002 (Year: 2002).*

Derwent abstract of JP-20021114849, original document published Apr. 2002 (Year: 2002).*

M.A. Rogers et al., Human Hair Keratin-Associated Proteins (KAPs). International Review of Cytology, 2006. 251: 209-263.

K. Khanbabaee et al., "Tannins: Classification and Definition", Nat. Prod. Rep., 2001, 18: 641-649.

H. Puchtler et al., "On the chemistry of formaldehyde fixation and its effects on immunohistochemical reactions". Histochemistry. 1985 82: 201-204.

http://ec.europa.eu/consumers/cosmetics/cosing/index.cfm?fuseaction=search.details_v2&id=92003 retrieved Nov. 17, 2017.

International Search Report and Written Opinion dated Oct. 8, 2018 for PCT/US2018/036002.

Database WPI Week 200260 Thomson Scientific, London, GB, XP002784247, 2002.

Database WPI Week 200647 Thomson Scientific, London, GB, XP002784248, 2006.

Database Caplus [online] Chemical Abstracts Service, Coumbus, Ohio, US, 1976, G.S. Gol'din et al.; "Polysiloxanepropyl meleates and study of their surface activity", XP002784249, Abstract only.

Database WPI Week 201632 Thomson Scientific, London, GB, XP002784250, 2015.

R. Wagner et al.: "Silicon-Modified-Carbohydrate-Surfactants-III: Catonic and Anionic Compounds", Applied Organometallic Chemistry, vol. 11, No. 6, Jun. 1, 1997, pp. 523-538, XP05501848.

Pinteala M et al: "Functional Polysiloxanes. 02. on the Reaction of Hydroxypropyl—and Aminoalkyl-Terminated Polydimethylsiloxanes With Cyclic Anydrides" Polymer Bulletin, SPinger, Heidelberg, DE, vol. 32, No. 2, Feb. 1, 1994, pp. 173-178, XP000425948.

Database WPI Week 199749 Thomson Scientific, London, GB, XP002784251, 1997.

Database Caplus [online] Chemical Abstracts Service, Coumbus, Ohio, US, 1977, Tanabe Seiyaku Co. Ltd. "Hair waving preperations containing unsaturated carboxylic acid amides and esters", XP002784252.

Database Caplus [online] Chemical Abstracts Service, Coumbus, Ohio, US, 1976, Tanabe Seiyaku Co. Ltd. "Hair waving preperations containing carboxylic acid esters or amides", XP002784253.

Database WPI Week 201837 Thomson Scientific, London, GB, XP002784254, 2018.

http://ec.europa.eu/consumers/cosmetics/cosing/index.cfm?fuseaction=search.details_v2&id=92003.

Tanabe Seiyaku CO et al.: "Hair Waving Preparation Containing Carboxylic Acid Esters or Amides" CAPLUS, Chemical Abstract Service, Columbus, OH, US, Jan. 1, 1976; XP002784253.

Pinteala M. et al.; Functional Polysiloxanes, 02. On the reaction of Hydroxypropyl- and Aminoalkyl-terminated Polydimethylsiloxanes with Cyclic Andhydrides, Polymer Bulletin, Springer, Heidelberg, DE, vol. 32, No. 2, Feb. 1, 1994, pp. 173-178 XP000425948.

International Search Report and Written Opinion dated Feb. 27, 2020.

M.A. Rogers, L. Langbein, S. Praetzel-Wunder, H. Winter, J. Schweizer, J. Int Rev Cytol. 2006; 251:209-6.

H. Puchtler et al., "On the chemistry of formaldehyde fixation and its effects on immunohistochemical reactions", Histochemistry, 82(1985), pp. 201-204.

L. Ladriere et al., Molecular and Cellular Biochemistry (1999), 198 (1&2), 35-139.

L. Ladriere et al., "Can glycrol-1,2,3-tris(methylsuccinate) stimulate insulin release after oral administration?"; Medical Science Research (1999), 27(5), 303-304.

L. Ladriere et al., "Assessment of the Nutritional Value of Glycerol-1,2,3-tris (methylsuccinate in Fed an Starved Rats"; Molecular Genetics and Metabolism (1999), 67(3), 254-260.

T. Zhang et al, Abstracts 44th Central Regional Meeting of the American Chemical Society, Mount Pleasant, MI, May 15-17, 2013, CERM-6.

N. R. Luman et al., Cover Picture: Chemistry—A European Journal (2003), 9(22), 5618-5626.

G. P. Andrews et al., "Branching Polyester Oligomers and Fractals"; ACS Symposium Series (2003), 834 8NMR Spectroscopy of Polymers in Solution and in the solid state), 216-227.

Pacifichem 2010; Abstract—The 2010 International; Honolulu, Chem. Eng. News Archieve; Dec. 15-20.

A. H. Fawcett et al, J. Pol. Sci., Part A: Polymer Chemistry (1994), 32(5). 815-827.

https://en.wikipedia.org/wiki/Sugar_alcohol.

Sugarhara et al.; "Effect of inorganic and organic counterions on interfacial properties of olelc acid-based gemini surfactants"; Colloids and Surfaces A; 538: (2018) 73-78.

Boschet al.; "Synethesis of Macrocyclic Dilactones through Lipases"; Department of Biological Organic Chemistry; (2005) 2611-2614.

Yang et al., "Hair Care Cosmetics"; Cosmetic Science and Technology: Theoretical Principles and Applications; Beauty Hi-tech Innovation Co., Chapter 36 (2017).

Z. Song, Z. Xiao, Linchan Huaxue Yu Gongye (1988), 8(3), 9-18.

T. Nagao, T. Sayuri, T. Tatsuya, M. Yukari, S. Hideaki Journal of Oleo Science (2011), 60(9), 457-62.

Karamali Khanababaee and Teunis van Ree, Nat. Prod. Rep., 2001, 18, 641-649 "Tannins: Classification and Definition".

Dr. Frederic Pilz, COSSMA (2010) vol. 7-8 p. 18.

"Practical Modern Hair Science" Trefor Evans and R. Randall Wichett, Alluredbooks, Carol Stream, Illinois, 2012.

* cited by examiner

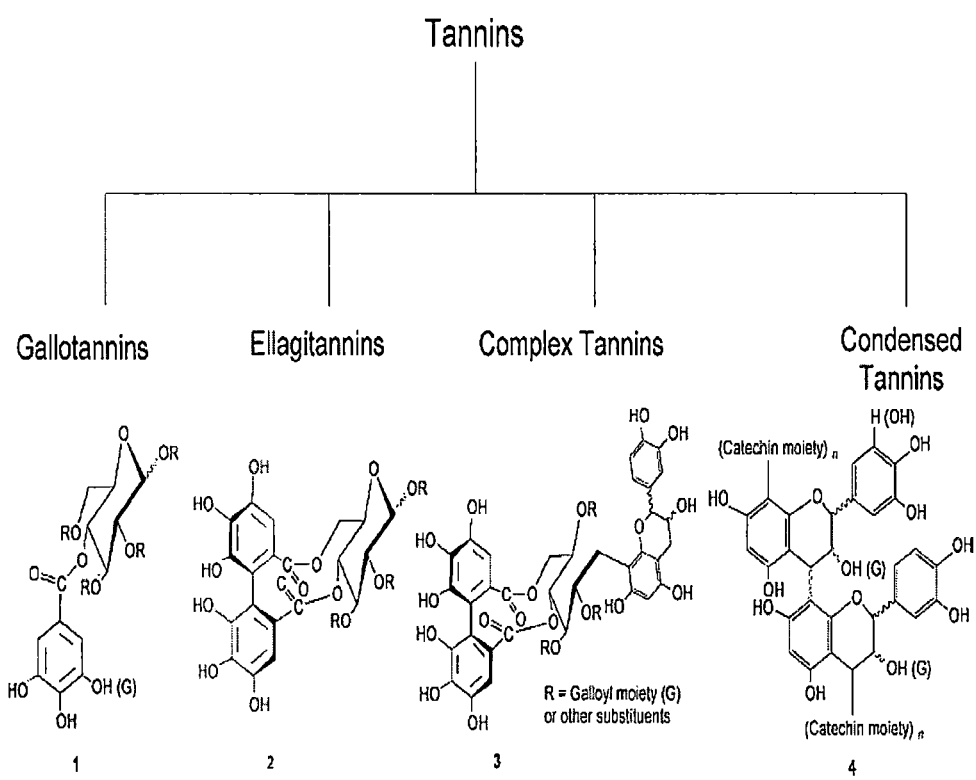

AQUEOUS COMPOSITIONS FOR THE TREATMENT OF HAIR

FIELD OF THE INVENTION

This invention relates to aqueous compositions for hair treatment, comprising polyorganosiloxanes A) or organic compounds B) having certain functional groups, in particular aldehyde and unsaturated dicarboxylic acid moieties, hair treatment or hair care compositions comprising the aqueous compositions, a process for the treatment of hair which comprises the steps of providing the aqueous compositions and applying said aqueous compositions to the hair, and the use of the aqueous compositions for the treatment of hair.

BACKGROUND OF THE INVENTION

Hair generally can be straight, wavy, curly, kinky or twisted. A human hair includes three main morphological components, the cuticle (a thin, outer-most shell of several concentric layers), the cortex (the main body of the hair), and, in case of higher diameter hair, the medulla (a thin, central core). The cuticle and cortex provide the hair strand's mechanical properties, that is, its tendency to have a wave, curl, or kink. A straight hair strand can resemble a rod with a circular cross-section, a wavy hair strand can appear compressed into an oval cross-section, a curly strand can appear further compressed into an elongated ellipse cross-section, and a kinky hair strand cross-section can be flatter still.

The primary component of hair is the cross-linked, alpha-helix protein keratin. Keratins are intermediate filament proteins found specifically in epithelial cells, e.g. human skin and hair, wool, feathers, and nails. The α-helical type I and II keratin intermediate filament proteins (KIFs) with molecular weights around 45-60 kDa are embedded in an amorphous matrix of keratin-associated proteins (KAPs) with molecular weights between 20 to 30 kDa (M. A. Rogers, L. Langbein, S. Praetzel-Wunder, H. Winter, J. Schweizer, J. Int Rev Cytol. 2006; 251:209-6); both intra- and intermolecular disulfide bonds provided by cystines contribute to the cytoskeletal protein network maintaining the cellular scaffolding. In addition to the disulfide cross-links ionic bonding or salt bridges which pair various amino acids found in the hair proteins contribute to the hair strand's outward shape.

It is known in the art that hair can be treated with functionalized silicones which deliver one or more cosmetic benefits, such as conditioning, shine and UV protection as well as color retention. Typically, these silicones are physically deposited on the fiber surface (cuticle) and therefore responsible for the outward appearance of the hair. They can be removed partially or completely by repeated washing processes. While the deposited silicones considerably improve the surface properties of hair, i.e. smoothness and friction, they do not substantially impact the shape, the mechanical properties and the release properties of the hair. Alternative hair treatment methods are available, but these often involve the use of harsh and regulated substances. There has been a need for efficient compounds for the treatment of hair which can be synthesized in a straight forward and cost efficient way, which are easy to formulate and easy to use, yielding long term stable formulations even in the presence of other performance ingredients and which are useful for strengthening of hair, for hair color retention, for hair color enhancement, for hair color protection, for shaping of hair, i.e. the curling and straightening of hair, for hair conditioning, for hair smoothening or softening, for hair straightening, and for improving manageability of the hair, in particular for improving the combability of the hair. In particular, benefits regarding the retention of artificial hair colours without the usage of strongly irritating auxiliaries should be achieved.

The present inventors found that aqueous compositions comprising polyorganosiloxanes A) or organic compounds B) which carry specific functional groups are suitable to satisfy the above need. The present invention accordingly provides aqueous compositions which can be synthesized in a straightforward and cost-efficient way, are easy to formulate and to use, and are useful for strengthening of hair, for hair color retention, for hair color enhancement, for hair color protection, for shaping of hair, i.e. the curling and straightening of hair, for hair conditioning, for hair smoothening or softening, for hair straightening, and for improving manageability of the hair, in particular for improving the combability of the hair. In particular, they avoid the usage of strongly irritating auxiliaries.

SUMMARY OF THE INVENTION

In accordance with the present invention, aqueous compositions for hair treatment are provided, comprising at least one polyorganosiloxane A) having an average number of 2 to 1000 siloxy units selected from the siloxy groups of the formulas:

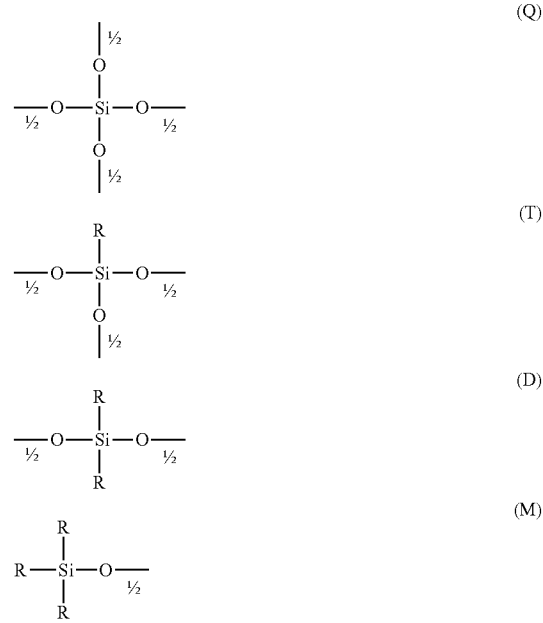

wherein
each R is independently selected from $R^1$ and $R^F$, wherein $R^1$ is selected from organic groups bound to the silicon atoms by a carbon atom, and two groups $R^1$ may form a bridging group between two silicone atoms, and $R^F$ is selected from organic groups different from $R^1$ and is bound to the silicon atoms by a carbon atom, which contain at least one functional group F selected from:

—O—C(O)—CH=CH—C(O)OH

—NH—C(O)—CH=CH—C(O)OH

—NR¹—C(O)—CH=CH—C(O)OH

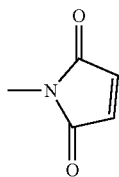

and

—O—C(O)—C(O)H, with the proviso that the polyorganosiloxane A) comprises at least one groups $R^F$ and/or
at least one organic compound B) having an average number of 2 to 100 carbon atoms selected from the formula:

$R^2$—$(F)_{2-18}$ wherein F is as defined above, and
$R^2$ is selected from divalent to octadecavalent hydrocarbon radicals which have up to 100 carbon atoms, and may contain optionally one or more groups selected from —O—, —NH—, —C(O)—, —C(S)—, tertiary amino groups

and quaternary ammonium groups

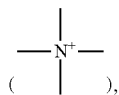

and wherein $R^2$ may optionally be substituted by one or more hydroxyl groups.

The present invention further provides aqueous compositions as defined herein, which are selected from a hair shampoo composition, hair care composition, hair condition composition, hair strengthening composition, hair coloration or dyeing composition, hair combability improving composition, anti-frizz composition, hair rinse-off and leave-on compositions, hair treatment or hair care compositions comprising the aqueous compositions as defined herein and a process for the treatment of hair which comprises the steps of providing an aqueous compositions as defined herein, and applying said aqueous compositions to said hair. Further the present invention relate to the use of the aqueous compositions as defined herein for the treatment of hair, and a method of hair treatment wherein the aqueous compositions as defined herein are brought into contact with hair, particular useful for strengthening of hair, for hair color retention, for hair color enhancement, for hair color protection, for shaping of hair, i.e. the curling and straightening of hair, for hair conditioning, for hair smoothening or softening, for hair straightening, for improving manageability of the hair, in particular for improving the combability of the hair.

BRIEF DESCRIPTION OF THE DRAWINGS

FIG. 1 is a chart of preferred tannins that may be used herein.

DETAILED DESCRIPTION OF THE INVENTION

The aqueous composition for hair treatment according to the invention comprises at least one polyorganosiloxane A) and/or at least one organic compound B), that is the aqueous composition may comprise the at least one polyorganosiloxane A) or the at least one organic compound B), or both of them.

The aqueous composition for hair treatment according to the invention comprises water, preferably in an amount of at least 1 weight-%, more preferably at least 5 weight-%, more preferably at least 10 weight-%, more preferably at least 15 weight-%, more preferably at least 20 weight-%, and preferably up to 95 weight-%, more preferably up to 90 weight-%, more preferably up to 85 weight-%, more preferably up to 80 weight-%, more preferably up to 75 weight-%, more preferably up to 70 weight-%, based on the total weight of the aqueous compositions.

In a preferred aqueous composition according to the invention the polyorganosiloxane A) comprises at least two groups $R^F$ per molecule.

Furthermore the aqueous composition according to the invention comprises preferably at least one surfactant, wherein the weight ratio of said surfactant to the polyorganosiloxane A) or the compound B) is preferably at least 0.06, more preferred 0.06 to 5, more preferred 0.06 to 3, even more preferred 0.1 to 3, specifically 0.1 to 2, more specifically 0.1 to 1.

The aqueous composition according to the invention preferably comprises from 0.1 to 20 wt-% preferably 0.5 to 15 wt-%, more preferably 1 to 10 wt-% of the polyorganosiloxane A) or the compound B) based on the weight of the aqueous composition. Aqueous compositions comprising mixtures of the polyorganosiloxane A) or the compound B) may comprise more than these amounts, e.g. up to 30 wt.-%, preferably 0.1 to 20 wt-%, more preferably 0.5 to 15 wt-%, and even more preferably 1 to 10 wt-%.

In the aqueous composition according to the invention in the polyorganosiloxane A), $R^F$ preferably is a group of the formula:

—$R^3$—F, wherein F is as defined above, i.e. selected from the groups consisting of:

—O—C(O)—CH=CH—C(O)OH

—NH—C(O)—CH=CH—C(O)OH

—NR¹—C(O)—CH=CH—C(O)OH

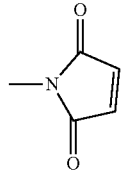

and

—O—C(O)—C(O)H, and R³ is selected from divalent hydrocarbon radicals which have up to 30 carbon atoms, which optionally contains one or more groups selected from —O—, —NH—, —C(O)—, —C(S)—, tertiary amino groups

and quaternary ammonium groups

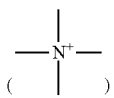

and wherein the divalent hydrocarbon radicals R³ optionally are substituted by one or more hydroxyl groups.

Generally the functional groups F are bound to a carbon atom in the groups $R^F$ or $R^3$ respectively.

In a preferred embodiment of the aqueous composition according to the invention in the polyorganosiloxane A) the molar portion of the siloxanyl units which contain the group $R^F$ to all siloxanyl units of the polyorganosiloxane A) is 3.33 to 100 mol %, more preferred 5 to 100 mol %, even more preferred 5 to 50 mol %, most preferred 10 to 50 mol %.

In another preferred embodiment of the aqueous composition according to the invention in the polyorganosiloxane A) the molar portion of branching T and Q moieties is 0 to 50%, preferred 0 to 20%, more preferred 0 to 10%, specifically 0 to 5%, more specifically 0% based on the number of all siloxy units.

The average number of siloxy units in the polyorganosiloxanes A) is 2 to 1000, preferred 2 to 300, more preferred 2 to 30, even more preferred 2 to 20, even more preferred 2 to 15, specifically 2 to 12, more specifically 2 to 7. The average number of siloxy units can be determined i.e. by GPC (Gel Permeation Chromatography) using a system calibration versus polystyrene standards.

Without wishing to be bound by any particular theory, it is believed that the presence of the double bond, which is activated by electron-withdrawing groups, in the group F is important for the invention as this double bond can react with sulfur containing groups present in keratin fibers. This reaction would lead to the straightening of the hairs and the silicone part would bring softness.

It is within the scope of the invention to use mixtures of different polyorganosiloxanes A) according to the invention. Mixtures of polyorganosiloxanes A) may yield bi-, tri- and higher modal molecular weight distributions, differing in the siloxane chain length. Mixtures of two polyorganosiloxanes A) having a bimodal distribution are preferred. One preferred embodiment of the invention is a mixture comprising short chained siloxanes bearing on average 2 to 15 siloxy units and longer chained siloxanes bearing on average 16 to 30 siloxy units. Such mixtures have the advantage that depending on the size of the molecules different locations within the hair structure can be modified with silicone polymers.

In the polyorganosiloxanes A) which are used in the present invention the organic radicals R attached to the siloxy units are selected from organic groups $R^1$ and the specific functionalized groups $R^F$ with the proviso that there must be at least one group $R^F$. Preferably the polyorganosiloxanes A) comprise at least two groups $R^F$ per polyorganosiloxane molecule.

The organic radicals $R^1$ are preferably selected from the group consisting of straight-chain, cyclic or branched, saturated, unsaturated or aromatic hydrocarbon radicals which have up to 100 carbon atoms which optionally contain one or more groups selected from —O—, —NH—, —C(O)—, —C(S)—, tertiary amino groups

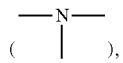

and quaternary ammonium groups

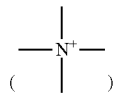

and which are optionally substituted by one more groups selected from the group consisting of hydroxyl, halogen (like chlorine, fluorine), a polyether radical with up to 60 carbon atoms, or two radicals $R^1$ from different siloxy moieties form a straight-chain, cyclic or branched, saturated, unsaturated or aromatic alkandiyl hydrocarbon radical which has 2 to 20 carbon atoms between two silicon atoms, which are optionally substituted by one or more hydroxyl groups or halogen atoms, and are linked to silicon by a carbon atom.

More preferably $R^1$ is selected from the group consisting of n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which optionally can be each substituted by hydroxyl and halogen, and which optionally can contain one or more ether groups (—O—).

Still more preferably, the radicals $R^1$ include: n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which can be substituted by one or more, preferred up to five, groups selected from hydroxyl and halogen, preferred fluorine, and can contain one or more ether groups, i.e. $H_3C$—, $CH_3CH_2$—, $CH_3CH_2CH_2$—, $(CH_3)_2CH$—, $C_8H_{17}$— and $C_{10}H_{21}$—, $H_2C$=CH—O—$(CH_2)_{1-6}$, cycloaliphatic radicals, i.e. cyclohexylethyl, limonyl, norbornenyl, phenyl, tolyl, xylyl, benzyl and 2-Phenylethyl, halogen($C_1$-$C_{10}$)alkyl, i.e. $C_fF_{fn+1}CH_2CH_2$— wherein f is 1 to 8, i.e. $CF_3CH_2CH_2$—, $C_4F_9CH_2CH_2$—, $C_6F_{13}CH_2CH_2$—, $C_2F_5$—O($CF_2$—$CF_2$—O)$_{1-10}CF_2$—,

F[CF(CF$_3$)—CF$_2$—O]$_{1-5}$—(CF$_2$)$_{0-2}$, $C_3F_7$—OCF(CF$_3$)— and $C_3F_7$—OCF(CF$_3$)—CF$_2$—OCF(CF$_3$)—. In the most preferred embodiment $R^1$ is selected from the group consisting of methyl, vinyl, phenyl, 3,3,3-trifluoropropyl, most preferred methyl.

$R^3$ in the polyorganosiloxane A) connecting the silicone atom and the functional group F as —$R^3$—F, is preferably selected from a divalent hydrocarbon radical which has up to 30 carbon atoms, which optionally contains one or more groups selected from —O—, —NH—, —C(O)—, —C(S)—, tertiary amino groups

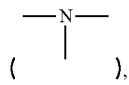

and quaternary ammonium groups

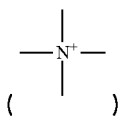

and wherein $R^3$ optionally is substituted by one or more hydroxyl groups. $R^3$ is preferably bound to silicon by a carbon atom.

In a preferred embodiment the group $R^3$ results from the reaction of epoxy-modified silicones with acids carrying the group F. Most preferred Si—H functional silicones are reacted with allyl glycidyl ether in a hydrosilylation reaction, and the resulting epoxy siloxane moiety of formula:

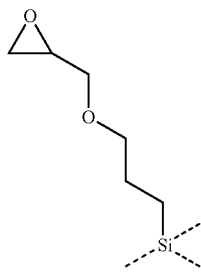

(dotted lines are free valencies of the silicon atom) is reacted with an acid to form —$R^3$—F being a group of the formula:

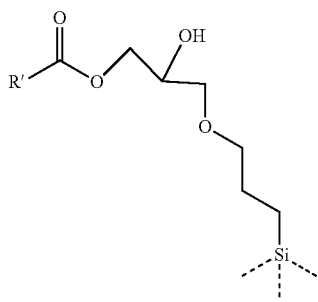

(dotted lines are free valencies of the silicon atom) with $R^1$ being selected from:

—CH=CH—C(O)OH and

—C(O)H.

In another preferred embodiment hydroxyalkylfunctional polyorganosiloxanes are reacted with maleic acid anhydride to obtain a compound having the functional group F being —O—C(O)—CH=CH—C(O)OH.

In a preferred embodiment the polyorganosiloxanes A) according to the invention contain at least two radicals of the formula $M^F$ and/or $D^F$:

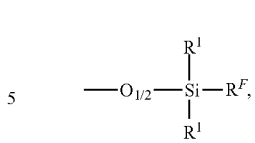

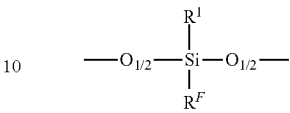

wherein $R^1$ and $R^F$ are as defined above.

In a preferred embodiment the polyorganosiloxanes according to the invention are selected from the formulas:

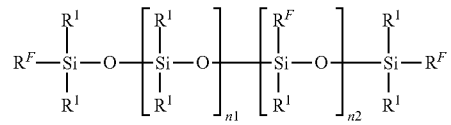

wherein $R^1$ and $R^F$ are as defined above, and n1+n2 is 0 to 28, preferred 0 to 20, more preferred 0 to 15, and n2 is preferably 0,

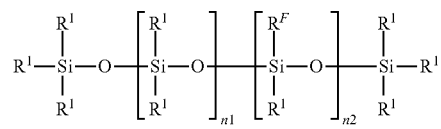

wherein $R^1$ and $R^F$ are as defined above, n1+n2 is 2 to 28, preferred 2 to 20, more preferred 2 to 15, even more preferred 5 to 15, with n2≥2, preferred 2 to 28, more preferred 2 to 10, even more preferred 2 to 5, and

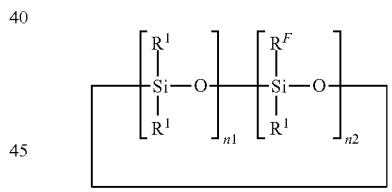

wherein $R^1$ and $R^F$ are as defined above, n1+n2 is 3 to 7 with n2≥2, preferred n1+n2 is 2 to 7, more preferred 2 to 5, even more preferred 3 to 5.

A particular preferred embodiment are α,ω-functionalized polyorganosiloxanes according to the following formula:

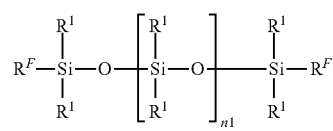

wherein n1 is 0 to 28, preferred 1 to 20, more preferred 1 to 15 and $R^1$ and $R^F$ are as defined above.

In a preferred embodiment the polyorganosiloxanes A) according to the invention have number-average molecular weights Mw<2000 g/mol, preferred <1500 g/mol, more preferred <1000 g/mol, as determined by GPC using polystyrene as standard.

In a preferred embodiment of the invention mixtures of more than one type of polyorganosiloxanes A) according to the invention are used.

In accordance with the present invention it is possible that the polyorganosiloxane A) in addition to the functionalized groups $R^F$ may carry further functional organic groups $R^{FA}$ which are selected from organic groups different from $R^1$ and $R^F$ and which contain at least one functional group FA selected from the group consisting of:
- an optionally substituted azetidine or azetidinium group,
- a methylol group,
- a mono-, di-, trihydroxy-substituted aromatic group,
- a thio ester and
- a thio ether group,
- alkoxy silyl group,
- amino group,
- ammonium group,
- phosphonium group,
- epoxy group,
- carbonate group,
- urethane group,
- isocyanate group, including blocked isocyanate group,
- urea group,
- amido group,
- aldehyde group,
- acetal or half acetal group,
- Schiff-Base or enamine group,
- zwitterionic group,
- carboxylic acid or carboxylate group,
- sulfonic acid or sulfonate group,
- sulfuric acid half ester or sulfate group,
- phosphoric acid ester or phosphate group,
- phosphonic acid ester or phosphonate group,
- phosphorous acid ester or phosphite group,
- xanthogenate/xanthogenate ester group,
- thiosulfato group,
- mercapto group,
- saccharide group, and
- polyether group with up to 60 carbon atoms.

Such functional groups FA may also replace the functional group F in the organic compound B) as long as there remains at least one group F in the compounds of formula $R^2$—$(F)_{2\text{-}18}$.

A particular preferred combination of the functional groups F and FA is a combination of —O—C(O)—C(O)H and a mono-, di-, trihydroxy-substituted aromatic group, such as with $R^{FA}$ having the structure:

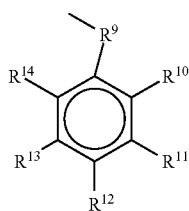

wherein
$R^9$ is selected from $R^3$ as defined above, with the additional possibility that $R^3$ is substituted by nitrogen containing groups, such as —$NH_2$, —$NHR^1$, —$N(R^1)_2$, wherein $R^1$ is as defined above, $R^{10}$, $R^{11}$, $R^{12}$, $R^{13}$, $R^{14}$ are the same or different from each other and are selected from hydroxyl and $R^2$, as defined above, with the proviso that 2 to 3 groups $R^{10}$ to $R^{14}$, more preferred 2 or 3 groups are hydroxyl (—OH).

A particularly preferred group $R^{FA}$ is

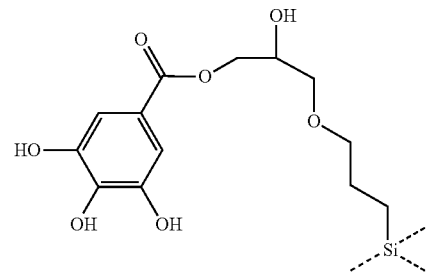

(dotted lines are free valencies of the silicon atom).

In another preferred embodiment of the present invention the polyorganosiloxanes A) according to the invention are combined with other functional polyorganosiloxanes having preferably functional groups selected from amino, quaternary ammonium, and quaternary phosphonium groups alone or optionally in combination with anionic polyorganosiloxane compounds having functional group selected from carboxylic acid/carboxylate, sulphonic acid/sulphonate, sulfuric acid half ester/sulphate, phosphoric acid ester/phosphate, phosphonic acid ester/phosphonate, phosphorous acid ester/phosphite, and xanthogenate-/xanthogenate ester. Examples for the above mentioned compounds are described in WO 2012/143371. It is also preferred to combine the polyorganosiloxanes according to the invention with betaine functional polyorganosiloxanes. Examples for these compounds are described in WO 2012/143371. It is further preferred to combine the polyorganosiloxanes according to the invention with di- and polycationic compounds of the ABA or block copolymer type. Examples for these compounds are described in WO 02/10257, WO 02/10259 and DE 10036553.

In a preferred embodiment of the invention the aqueous compositions according to the invention comprises at least one surfactant which is preferably selected from cationic, nonionic, betaine and anionic surfactants, preferably having a HLB value ranging from 1 to 20, preferred 7 to 20, more preferred 8 to 20. More preferably the surfactant is selected from hydrocarbon based or silicone based emulsifiers each being different from polyorganosiloxane A) and compound B). The amount of the surfactant in the aqueous compositions according to the invention is preferably from about 0.05% to about 15%, more preferably from about 0.05% to about 5%, still more preferably from about 0.1% to about 5%, specifically from 0.1 to 3% by weight of the aqueous composition.

The weight ratio of the surfactant to the polyorganosiloxanes A) preferably is at least 0.06, preferred 0.06 to 5, more preferred 0.06 to 3, even more preferred 0.1 to 3, specifically 0.1 to 1.

Depending on the chemical nature of the continuous and discontinuous phase emulsifiers having a HLB value <7 (W/O emulsion type) or >7 (O/W emulsion type) are preferably selected.

In a preferred embodiment of the invention the hair treatment composition provided is a W/O emulsion (preferably a water-in-oil-emulsion (W/O-emulsion)).

In another preferred embodiment of the invention the hair treatment composition provided is an O/W formulation (preferably an oil-in-water-emulsion (O/W-emulsion)).

Preferred examples for hydrocarbon based emulsifiers are cationic, nonionic, betaine and anionic emulsifiers.

The cationic surfactant is preferably selected from primary, secondary, or tertiary amine compounds having up to 50 carbon atoms and salts thereof, amido amine compounds having up to 50 carbon atoms and salts thereof, such as behenamidopropyl dimethylamine and quaternary ammonium compounds, having up to 50 carbon atoms, and preferably with up to 20 carbon atoms in the alkyl groups thereof, such as tetraalkyl ammonium compounds, e.g. hexadecyl-trimethylammonium salts, dimethyldioctadecylammonium salts, distearyldimethylammonium salts, cetrimonium salts, cetylpyridinium salts, alkylbenzyldimethylammonium salts such as benzalkonium salts, benzethonium salts, ester quats having at least one quaternary ammonium group and at least one ester group.

Further preferred examples for cationic emulsifiers are quaternary ammonium groups or amino groups containing linear or branched C8 to C50, preferred C8 to 40, more preferred C8 to C30 alkyl, fatty alcohol and fatty acid based emulsifiers, i.e. fatty acid based ester quats containing one or two fatty acid moieties, fatty amines and ethoxylated/propoxylated fatty amines.

Preferably, the cationic surfactant is a mono-long alkyl -tri short alkyl quaternized ammonium salt or di-long alkyl -di short alkyl quaternized ammonium salt wherein one or two alkyl substituents are selected from an aliphatic group of from about 8 to about 30 carbon atoms or an aromatic, alkoxy, polyoxyalkylene, alkylamido, hydroxyalkyl, aryl or alkylaryl group having up to about 30 carbon atoms; the other alkyl groups are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and the counter ion is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 8 carbons, or higher, can be saturated or unsaturated.

Preferably, one alkyl group is selected from an alkyl group of from about 8 to about 30 carbon atoms, more preferably from about 14 to about 26 carbon atoms, still more preferably from about 14 to 22 carbon atoms; the other alkyl groups are independently selected from the group consisting of —$CH_3$, —$C_2H_5$, —$C_2H_4OH$, —$CH_2C_6H_5$, and mixtures thereof; and the counter ion is selected from the group consisting of $Cl^-$, $Br^-$, $CH_3OSO_3^-$, and mixtures thereof. It is believed that such mono-long alkyl quaternized ammonium salts can provide, in addition to their emulsification capability, improved slippery and slick feel on wet hair, compared to multi-long alkyl quaternized ammonium salts. It is also believed that mono-long alkyl quaternized ammonium salts can provide improved hydrophobicity and smooth feel on dry hair, compared to amine or amine salt cationic surfactants.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride.

Preferred cationic surfactants are saturated or unsaturated fatty acid based mono-ester and di-ester quats (quats=quaternary ammonium cation comprising compound) having 10 to 18 carbon atoms in the alkyl chain. Commercially available examples are Arquad PC SV-60 PG and Armocare VGH70 (Akzo Nobel).

Details on cationic surfactants are disclosed in US2013/259820.

The aqueous compositions of the present invention preferably comprise the cationic surfactant in amount of from about 0.05% to about 15%, preferably from about 0.05% to about 5%, still more preferably from about 0.1% to about 5%, specifically from 0.1 to 3% by weight of the composition.

Preferred examples for nonionic emulsifiers are ethylene oxide (EO), propylene oxide (PO) and butylene oxide (BO) containing linear or branched C8 to C50, preferred C8 to 40, more preferred C8 to C24 fatty alcohol and fatty acid based emulsifiers as well as saccharide based emulsifiers, i.e. alkyl glycosides, alkoxylated fatty acid sorbitane esters and fatty acid glucamides. Another variety of preferred nonionic surfactants are the semi-polar amine oxides, phosphine oxides, and sulfoxides.

Preferred nonionic surfactants are saturated or unsaturated natural alcohol based ethoxylates having 10 to 18 carbon atoms in the alkyl chain and 5 to 80 EO units. Commercially available examples are the Genapol C, LA, V, O and T types (Clariant).

Preferred nonionic surfactants are linear or branched oxo alcohol based ethoxylates having 11 to 17 carbon atoms in the alkyl chain and 5 to 100 EO units. Commercially available examples are the Genapol UD, OA, OX, X, LCN types (Clariant).

Preferred nonionic surfactants are saturated or unsaturated alcohol based block ethoxylates-propoxylates having 10 to 18 carbon atoms in the alkyl chain and 2 to 20 EO units. Commercially available examples are the Genapol EP types (Clariant).

Preferred nonionic surfactants are ethoxylate-propoxylate block copolymers containing 5 to 70% wt % EO units. Commercially available examples are the Genapol PF and PH types (Clariant).

Preferred nonionic surfactants are saturated or unsaturated fatty acid based ethoxylates having 10 to 18 carbon atoms in the alkyl chain and 5 to 100 EO units. Commercially available examples are the Genagen O and S types (Clariant).

Preferred nonionic surfactants are saturated or unsaturated fatty acid based castor oil ethoxylates having 10 to 18 carbon atoms in the alkyl chains and 5 to 80 EO units. Commercially available examples are the Emulsogen HCO and EL types (Clariant).

Preferred nonionic surfactants are saturated or unsaturated fatty acid derivatized oligoglycerines. Preferred examples are fatty acid derivatized di-, tri, or tetraglycerines, i.e. mono- or diesters of diglycerine having 10 to 18 carbon atoms in the alkyl chain and optionally 5 to 100 EO units. Commercially available examples are the Hostacerine types (Clariant).

Preferred nonionic surfactants are saturated or unsaturated fatty acid sorbitane ester based ethoxylates having 10 to 18 carbon atoms in the alkyl chain and 5 to 50 EO units attached to the sorbitane ring. A commercially available example is Emulsogen 4156 (Clariant).

Preferred nonionic surfactants are saturated or unsaturated alcohol based glycosides having 8 to 18 carbon atoms in the alkyl chain and 1 to 10 glycosyl units. Commercially available examples are Plantacare 818up and 1200up (BASF).

Preferred nonionic surfactants are saturated or unsaturated fatty acid based glucamides, preferred fatty acid N-methylglucamides, having 8 to 18 carbon atoms in the alkyl chain. A commercially available example is the MEGA-10 type (Avanti).

Preferred nonionic surfactants are saturated or unsaturated fatty acid based alkanolamides, preferred fatty acid based ethanolamides, having 8 to 18 carbon atoms in the alkyl chain. Commercially available examples are the Aminon C types (Kao).

Preferred nonionic surfactants are the fatty amine or fatty acid amide based amine oxides having 8 to 30 carbon atoms in the alkyl chain. Commercially available examples are the Tomamine AO types (Air products) and the Genamineox types (Clariant).

The aqueous compositions of the present invention preferably comprise the nonionic surfactant in amount of from about 0.05% to about 15%, preferably from about 0.05% to about 5%, still more preferably from about 0.1% to about 5%, specifically from 0.1 to 3% by weight of the composition.

Preferred examples for betaine emulsifiers are carbobetaine, sulfobetaine, phosphatobetaine and phosphonatobetaine groups containing linear or branched C8 to C50, preferred C8 to 40, more preferred C8 to C30 alkyl, fatty alcohol and fatty acid based emulsifiers, i.e. cocoamidopropyl carbobetaines.

Preferably, suitable betaine surfactants for use in compositions according to the invention include those which are known for use in shampoo or other personal care cleansing. They include those surfactants broadly described as derivatives of aliphatic secondary and tertiary amines in which the aliphatic radical can be straight or branched chain and wherein one of the aliphatic substituents contains from about 8 to about 30 carbon atoms and one contains an anionic group such as carboxy, sulfonate, sulfate, phosphate, or phosphonate. Exemplary amphoteric surfactants for use in the formulations of the present invention include cocoamphoacetate, cocoamphodiacetate, lauroamphoacetate, lauroamphodiacetate, and mixtures thereof. They also include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 30 carbon atoms and one contains an anionic group such as carboxy, sulfonate, sulfate, phosphate or phosphonate.

Preferred carbobetaine surfactants are saturated or unsaturated fatty acid based sarcosides having 10 to 18 carbon atoms in the alkyl chain. A commercially available example is Medialan LD (Clariant).

Preferred carbobetaine surfactants are saturated or unsaturated fatty acid based amido propyl betaines having 10 to 18 carbon atoms in the alkyl chain. A commercially available example is Genagen CAB (Clariant).

Preferred sulfobetaine surfactants are saturated or unsaturated fatty acid based taurides having 10 to 18 carbon atoms in the alkyl chain. A commercially available example is Hostapon CT (Clariant).

Details on betaine surfactants are disclosed in US2015/011449.

The compositions of the present invention preferably comprise the betaine surfactant in amount of from about 0.05% to about 15%, preferably from about 0.05% to about 5%, still more preferably from about 0.1% to about 5%, specifically from 0.1 to 3% by weight of the composition.

Preferred examples for anionic emulsifiers are carboxylate, sulfate, sulfonate, phosphate and phosphonate groups containing linear or branched C8 to C50, preferred C8 to 40, more preferred C8 to C24 alkyl, fatty alcohol and fatty acid based emulsifiers, i.e. C8 to C24 fatty acid carboxylates, C8 to C24 fatty acid polyether carboxylates, C8 to C24 fatty acid polyether sulfates, C8 to C24 maleic acid addition products, C8 to C24 fatty alcohol sulfates, C8 to C24 sulfonates, C8 to C40 phosphates containing one or two fatty acid moieties.

Preferably, anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate; monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment of the present invention, the anionic surfactant is sodium lauryl sulfate or sodium laureth sulfate (sodium lauryl ether sulfate).

Preferred anionic surfactants are saturated or unsaturated fatty alcohol based polyether sulfates having 10 to 18 carbon atoms in the alkyl chain and 2 to 30 EO units. Commercially available examples are the Emulsogen EPM types (Clariant).

Preferred anionic surfactants are saturated or unsaturated fatty alcohol based polyether carboxylates having 10 to 18 carbon atoms in the alkyl chain and 2 to 30 EO units. Commercially available examples are the Empicol types (Huntsman).

Details on anionic surfactants are disclosed in US2015/011449.

Soaps include in particular salts of fatty acids such as alkaline or earth alkaline metal salts, such as sodium or potassium or calcium salts of C6 to C22 fatty acids, such as those obtained from saponification of triglycerides, e.g. alkaline or earth alkaline metal salts of lauric acid, myristic acid, palmitic acid, stearic acid, oleic acid, linoleic acid, linolenic acid.

The compositions of the present invention preferably comprise the anionic surfactant in amount of from about 0.05% to about 15%, preferably from about 0.05% to about 5%, still more preferably from about 0.1% to about 5%, specifically from 0.1 to 3% by weight of the composition.

Further details on surfactants are disclosed in US 2009-0165812.

Preferred examples for silicone based emulsifiers are cationic, nonionic, betaine and anionic emulsifiers.

Preferred examples for cationic emulsifiers are quaternary ammonium groups containing emulsifiers of the ABA type with EO/PO moieties attached to the terminal quat (quaternary ammonium cation comprising) ends of a silicone chain (WO2009/042083) or quaternized emulsifiers having polyether moieties attached to the silicone chain in a comb like arrangement (US2008/213208).

In another preferred embodiment of the invention hydrophilic polyhydroxy moieties as well as oleophilic fatty alkyl or fatty alkyl ester moieties are attached to the silicone chain (US2012/289649). A commercially available example for this type of W/O emulsifier is Silform® EOF (available from Momentive Performance Materials).

The compositions of the present invention preferably comprise the silicone based cationic surfactant in amount of from about 0.05% to about 15%, preferably from about 0.05% to about 5%, still more preferably from about 0.1% to about 5%, specifically from 0.1 to 3% by weight of the composition.

Preferred examples for siloxane based nonionic emulsifiers are ethylene oxide (EO), propylene oxide (PO) and butylene oxide (BO) containing emulsifiers of the ABA type with EO/PO/BO moieties attached to the terminal ends of a silicone chain or emulsifiers having polyether moieties attached to the silicone chain in a comb like arrangement. A commercially available example is SF 1540 (available from Momentive Performance Materials). In another preferred embodiment of the invention, hydrophilic polyether moieties as well as oleophilic alkyl chains are attached to the silicone chain (U.S. Pat. No. 4,698,178). In another preferred embodiment of the invention, hydrophilic polyglycerol moieties as well as alkyl or fatty alcohol ether/fatty acid ester moieties are attached to the silicone chain (US2010/0266651, US2009/0062459). In another preferred embodiment of the invention amodimethicone glycerocarbamates are used (Dr. Frederic Pilz, COSSMA (2010) vol. 7-8 p18 and WO 2013017260 A1). In another preferred embodiment of the invention, cetyl diglyceryl tris(trismethylsiloxy)silylethyl dimethicones are used (http://ec.europa.eu/consumers/cosmetics/cosing/index.cfm?fuseaction=search.details_v2&id=92003).

The latter four types of emulsifier are especially preferred for W/O emulsions.

The compositions of the present invention preferably comprise the silicone based nonionic surfactant in amount of from about 0.05% to about 15%, preferably from about 0.05% to about 5%, still more preferably from about 0.1% to about 5%, specifically from 0.1 to 3% by weight of the composition.

The compositions of the present invention preferably comprise the silicone based betaine and anionic surfactant in amount of from about 0.05% to about 15%, preferably from about 0.05% to about 5%, still more preferably from about 0.1% to about 5%, specifically from 0.1 to 3% by weight of the composition.

It is within the scope of the invention to use more than one surfactant in order to optimize the formulation stability. The total amount on surfactants in the compositions of the present invention preferably ranges from about 0.05% to about 15%, preferably from about 0.05% to about 5%, still more preferably from about 0.1% to about 5%, specifically from 0.1 to 3% by weight of the composition.

In a further embodiment of the invention the aqueous compositions optionally comprise additional additives, such as a) organic diluents or solvents,
b) proteins, preferably keratin,
c) emollients or fatty substances,
d) preservatives,
e) skin protecting ingredients,
f) conditioning agents,
g) oxidizing agents,
h) reducing agents,
i) tannins,
j) metal salts,
k) further auxiliaries selected from pH adjusting agents, thickeners (such as polysaccharide thickeners, starch, modified starches, xanthan, gellan, carragenan, pullulan, cellulose, cellulose derivatives, polyacrylic acids, polyacrylates copolymers, polyacrylamides, pectins, clays, fumed silica), lipids, amino acids, sugars, fragrances, sunscreen agents, vitamins, pearlescent agents, gelling agents, trace elements, sequestering agents, antioxidants, humectants, anti-hair loss agents, anti-dandruff agents, propellants, ceramides, polymers, in particular film-forming polymers, fillers, nacres, colorants, in particular pigments and dyes, and mixtures thereof, with the proviso that oxidizing agents and reducing agents are not present simultaneously in a given formulation.

Preferably, the hair strengthening compositions comprise the following components:

| Ingredient | Weight-% |
| --- | --- |
| polyorganosiloxane A) and/or compound B) | 0.05 to 30, preferably 1 to 10 |
| hydrocarbon or silicone based surfactant | 0 to 15, preferably 0.05 to 5 |
| Water | q.s. to add to 100% |
| diluents/solvents | 0 to 95, preferably 0.1 to 90 |
| protein, preferred keratin | 0 to 15, preferably 0 to 10, such as 0.01 to 5 |
| emollients/fatty substance | 0 to 15, preferably 0 to 10, such as 0.01 to 5 |
| Preservatives | 0 to 5, preferably 0 to 3, such as 0.01 to 2.5 |
| skin protecting ingredients | 0 to 15, preferably 0 to 10, such as 0.01 to 5 |
| conditioning agents | 0 to 15, preferably 0 to 10, such as 0.01 to 5 |
| oxidizing agents | 0 to 15, preferably 0 to 10, such as 0.01 to 5 |
| reducing agents | 0 to 15, preferably 0 to 10, such as 0.01 to 5 |
| tannins | 0 to 15, preferably 0 to 10, such as 0.01 to 5 |
| metal salts, | 0 to 15, preferably 0.01 to 10, such as 0.01 to 5 |
| hair dyeing agent | 0 to 15, preferably 0 to 10, such as 0.01 to 5 |
| other auxiliary agents | 0 to 15, preferably 0 to 10, such as 0.01 to 5 | wherein the wt-percentages relate to the complete weight of the aqueous compositions, and the individual wt-ranges may relate to a single component of the said class of components, but preferably relates to the total weight of each components of the said class of components.

In a preferred embodiment of the invention, the hair treatment formulations (which term is used as a synonym for the aqueous composition for hair treatment according to the present invention in this text) comprise the polyorganosiloxane A) or the compound B) in a concentration range from 0.05 to 30%, preferred 0.5 to 30%, more preferred 1 to 30%, even more preferred 1 to 20%, specifically 1 to 10%, wherein each percentage is per weight based on the total weight of the aqueous composition.

In a preferred embodiment of the invention the hair treatment formulations comprise the surfactants in a concentration range from 0 to 15%, preferred 0.05 to 15%, more preferred 0.1 to 5%, even more preferred 0.1 to 3%, wherein each percentage is per weight based on the total weight of the aqueous composition.

In a preferred embodiment of the invention the hair treatment formulations optionally comprise the diluents/solvents in a concentration range from 0.1 to 95%, preferred 10 to 95%, more preferred 20 to 95%, even more preferred 20 to 50% and 50 to 95%, wherein each percentage is per weight based on the total weight of the aqueous composition. In a preferred embodiment the hair treatment formulations do not comprise ethanol.

In a preferred embodiment of the invention the hair treatment formulations optionally comprise the protein, preferred keratin in a concentration range from 0 to 15%, preferred 0 to 10%, more preferred 0 to 5%, wherein each percentage is per weight based on the total weight of the aqueous composition.

In a preferred embodiment of the invention the hair treatment formulations optionally comprise the emollients/fatty substance in a concentration range from 0 to 15%, preferred 0 to 10%, more preferred 0 to 5%, wherein each percentage is per weight based on the total weight of the aqueous composition.

In a preferred embodiment of the invention the hair treatment formulations optionally comprise the preservatives in a concentration range from 0 to 5%, preferred 0 to 3%, more preferred 0 to 2%, even more preferred 0 to 1%, wherein each percentage is per weight based on the total weight of the aqueous composition.

In a preferred embodiment of the invention the hair treatment formulations optionally comprise the skin protecting ingredients in a concentration range from 0 to 15%, preferred 0 to 10%, more preferred 0 to 5%, even more preferred 0 to 1%, specifically 0 to 0.1%, wherein each percentage is per weight based on the total weight of the aqueous composition.

In a preferred embodiment of the invention the hair treatment formulations optionally comprise the conditioning agents in a concentration range from 0 to 15%, preferred 0 to 10%, more preferred 0 to 5%, even more preferred 0 to 1%, specifically 0 to 0.1%, wherein each percentage is per weight based on the total weight of the aqueous composition.

In a preferred embodiment of the invention the hair treatment formulations optionally comprise the oxidizing agents in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise the reducing agents in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise tannins in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise metal salts such iron or zinc salts in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise hair dyeing agents in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise the other auxiliary agents, which are commonly known for hair care compositions and are different from the aforementioned additives, in a concentration range from 0 to 15%, preferred 0 to 10%, more preferred 0 to 5%, even more preferred 0 to 2%, wherein each percentage is per weight based on the total weight of the aqueous composition.

The above described aqueous hair treatment formulations according to the invention can provide particularly benefits with respect to an improved durability of artificial colors on hair. In addition the aqueous hair treatment formulations according to the invention provide a hair strengthening and shaping effect as well as a conditioning effect, in particular, before, during and after a hair dyeing treatment, such as hair bleaching treatment.

Diluents/Solvents

The term "diluents/solvents" refers to substances that may be used to dilute/solvatize the at least one polyorganosiloxane A) and/or the at least one organic compound B) according to the invention and the other optional other ingredients as mentioned before in addition to water. Suitable organic solvents are i.e. 2-methyl-1,3-propanediol, mono and dialcohols or the ethers and esters thereof, in particular mono-C1-C3-alkyl ether, ethanol, n-propanol, isopropyl alcohol, tert. butanol, 1-methoxypropanol, 1-ethoxypropanol and ethoxydiglycol, diols and their ethers and esters, 1,3- and 1,4-butanediol, pentylene glycol, hexylene glycol, diethyleneglycol and the monomethyl and monoethyl ether thereof, dipropylene glycol and the monomethyl and monoethyl ether thereof, glycerol, diglycerol, hexanetriol, sorbitol, ethyl carbitol, benzyl alcohol, benzyloxy ethanol, propylene carbonate, N-alkyl pyrrolidone. In a preferred embodiment water/ethanol, water/isopropyl alcohol, water/dipropylene glycol and water propylene glycol mono methyl ether mixtures are used. Generally, the addition of certain amounts of short chained alcohols improves the homogeneity of the formulations and the penetration of the formulations into the hair. Depending on the polymer structure type and the application purpose certain quantities on acids, bases and/or short chained alcohols are required in order to get transparent formulations. Suitable acids include inorganic or organic acids, like for example carboxyl acids, like acetic acid, hydrochloric acid, sulfuric acid, phosphoric acid. Suitable bases include aqueous ammonia, alkaline hydroxides, alkaline carbonates, etc.

Protein/Keratin

The optional protein, preferred keratin protein fractions used comprise hydrolyzed keratin produced by alkaline and/or enzymatic hydrolysis using methods known in the art. The keratin hydrolysate is about 1,000-3,000 molecular weight. The keratin may be derived from human or other mammalian sources such as goat hair (US 2007-0048235), hoof or horn meals, (U.S. Pat. No. 6,555,505). Alternatively, "keratin protein fraction" is a purified form of keratin that contains predominantly, although not entirely, one distinct protein group as described in U.S. Pat. No. 7,148,327. Details on the keratin and keratin fractions are disclosed in US 2009-0165812.

Emollients, Fatty Substances

A further optional ingredient of the hair treatment formulations is one or more emollients. An "emollient" is a material that protects against wetness or irritation, softens, soothes, supples, coats, lubricates, moisturizes, protects and/or cleanses the skin. Emollients used comprise one or more of: a silicone compound, i.e. dimethicones, cyclomethicones, preferred $D_5$ and $D_6$ cyclosiloxanes, dimethicone copolyols or mixtures of cyclomethicones and dimethicone/vinyldimethicone cross polymer), polyols such as sorbitol, glycerin, propylene glycol, ethylene glycol, polyethylene glycol, caprylyl glycol, polypropylene glycol, 1,3-butane diol, hexylene glycol, isoprene glycol, xylitol, ethylhexyl palmitate, a triglyceride such as caprylic/capric triglyceride and fatty acid ester such as cetearyl isononanoate or cetyl palmitate. Details on emollients are disclosed in US 2009/0165812.

As fatty substances that are liquid at ambient temperature, often referred to as oils, that can be used in the invention, mention may be made of: hydrocarbon-based oils of animal origin, such as perhydrosqualene, hydrocarbon-based plant oils, such as liquid triglycerides of fatty acids containing 4 to 10 carbon atoms, for instance heptanoic or octanoic acid triglycerides, or else sunflower oil, maize oil, soya oil, grapeseed oil, sesame oil, apricot oil, macadamia oil, castor oil, avocado oil, caprylic/capric acid triglycerides, jojoba oil, shea butter; linear or branched hydrocarbons of mineral or synthetic origin, such as liquid paraffins and derivatives thereof, petroleum jelly, polydecenes, hydrogenated polyisobutene such as Parleam®; synthetic esters and ethers, in particular of fatty acids, for instance purcellin oil, isopropyl myristate, 2-ethylhexyl palmitate, 2-octyldodecyl stearate, 2-octyldodecyl erucate, isostearyl isostearate, hydroxylated esters, for instance isostearyl lactate, octyl hydroxystearate, octyldodecyl hydroxystearate, diisostearyl malate, triisocetyl citrate, fatty alcohol heptanoate, octanoate and decanoate; polyol ester, for instance propylene glycol dioctanoate, neopentyl glycol diheptanoate, diethylene glycol diisononanoate, pentaerythritol esters, fatty alcohols having 12 to 26 carbon atoms, for instance octyldodecanol, 2-butyloctanol, 2-hexyldecanol, 2-undecyl pentadecanol, oleyl alcohol, partially hydrocarbon-based and/or silicone-based fluoro oils, silicone oils, for instance volatile or non-volatile, linear or cyclic polydimethylsiloxanes (PDMS) which are liquid or pasty at ambient temperature (25° C.), such as cyclomethicones, dimethicones, optionally comprising a phenyl group, for instance phenyl trimethicones, phenyl trimethylsiloxydiphenylsiloxanes, diphenylmethyl-dimethyltrisiloxanes, diphenyl dimethicones, phenyl dimethicones, polymethylphenylsiloxanes; mixtures thereof. Details on suitable fatty substances are disclosed in WO 2012-038334.

Preservatives

Optionally, one or more preservatives may be included in the hair treatment formulations. Examples of such preservatives comprise one or more glycerin containing compound (e.g., glycerin or ethylhexylglycerin or phenoxyethanol), lactic acid, benzyl alcohol, EDTA, potassium sorbate and/or grapefruit seed extract. In a preferred embodiment, the hair straightening formulations are paraben free. Details on preservatives are disclosed in US 2009/0165812.

Skin Protecting Agents

Optionally, the hair treatment formulations comprise one or more skin protecting agents. Skin protecting agents comprise one or more agents that prevent the undesired transmission of microbes or organic/inorganic chemicals. Details on skin protecting agents are disclosed in US 2009/0165812.

Conditioning Agents

Optionally, one or more conditioning agent may be included in the hair treatment formulations. In one preferred embodiment silicone based conditioning agents are incorporated. Preferred materials are PDMS grades ranging from 10 to 1.000.000 mPa·s, C2 to C18-alkyl derivatized silicones, dimethiconols, polyether modified silicones, amino groups or quaternized ammonium groups containing silicones. They may be also selected from polyorganosiloxanes having functional groups FA as defined above. These silicones can be incorporated as neat materials, organic solutions, emulsions or microemulsions.

Preferred examples for quaternary ammonium groups (quats) containing conditioning agents are $\alpha,\omega$-quat group terminated silicones (U.S. Pat. No. 4,891,166), quat group terminated T shaped silicones (US2008027202), $\alpha,\omega$-silicone block terminated quats (WO02/10256) and silicones containing quat groups in a comb like arrangement, optionally containing additional moieties, i.e. polyethers or aromatic structures (US2008213208, U.S. Pat. Nos. 5,098,979, 5,153,294, 5,166,297, US2006188456). Other preferred examples are quat group/silicone block based copolymers (EP282720, U.S. Pat. Nos. 6,240,929, 6,730,766, DE102004002208). In another preferred embodiment quat group/silicone block/hydrophilic block based copolymers are used (WO 02/10257 and WO 02/10259, U.S. Pat. Nos. 7,563,856, 7,563,857, US20110039948, US2007106045, US2005255073, WO2004069137). Other preferred examples are quat group/silicone block based copolymers and quat group/silicone block/hydrophilic block based copolymers bearing terminal monofunctional silicone moieties (WO2013148629, WO2013148635, WO2013148935). In another preferred embodiment of the invention quat group terminated silicones bearing pending amino groups are used (DE10253152). Other preferred examples are silicone betaines (DE10036522, DE10036532). Commercially available examples for quaternary ammonium groups containing siloxanes are Silsoft Silk and Silsoft Q (available from Momentive Performance Materials).

The above described silicone based conditioning agents in particular impart a smooth and silky feel to hair.

Alternatively, hydrocarbon based conditioning agents can be included. Details on these cationic types of material, containing amino and/or quaternary ammonium groups are disclosed for example in US 2009/0000638 and WO 2012/027369.

Oxidizing Agents

Optionally, one or more oxidizing agent may be included in the hair treatment formulations. Preferred oxidizing agents include organic oxidizers, i.e. benzoquinone, other quinone derivatives including hydroquinone and aminoquinones and suitable organic peroxides. Details on organic oxidizers are disclosed in US 2012/0031420 and WO 2012/027369. Hydrogen peroxide is the preferred inorganic oxidizing agent. Persulfates, in the form of their sodium potassium and ammonium salts, may also be used alone or in combination with the hydrogen peroxide just before use. Other possible oxidizing agents include sodium percarbonate, sodium perborate, magnesium perborate, magnesium dioxide and barium dioxide. Details on these oxidizing agents are disclosed in U.S. Pat. No. 6,544,499.

Reducing Agents

Optionally, one or more reducing agent may be included in the hair treatment formulations with the proviso that oxidizing agents and reducing agents are not present simultaneously in a given formulation. Preferred reducing agents are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycollate, 1,2-propyleneglycol monothioglycollate (see also WO 93/1791), 1-3-propanediol monothioglycollate or the isomer mixture resulting therefrom, 1,3-butanediol and 1,4-butanediol monothioglycollate and the isomer mixtures therefrom, polyethylene glycol, such as di-, tri- and tetraethyleneglycol monothioglycollates, glycerol monothiolactate and further thio acids and the esters thereof, as well as mixtures thereof. Details on these organic reducing agents are disclosed in US 2009/0000638.

The usage of inorganic reducing sulfur compounds is basically also possible. Representative examples for use in the reducing compositions include cosmetically acceptable salts (e.g., alkali metal (e.g., sodium and potassium) and ammonium salts), esters (e.g., lower alkyl amines (e.g., triethanolamine (TEA), monoethanolamine (MEA) and aminomethyl propanol (AMP), of sulfite, disulfite, bisulfite, metabisulfite, hydrosulfite, hyposulfite and pyrosulfite). Specific examples of suitable reducing agents thus include sodium metabisulfite, potassium metabisulfite, sodium sulfite, potassium sulfite, sodium thiosulfate, potassium thiosulfate, ammonium bisulfite, ammonium sulfite, ammonium metabisulfite, MEA sulfite, MEA metabisulfite, potassium bisulfite, sodium bisulfite, ammonium bisulfite, sodium hydrosulfite, potassium hydrosulfite, ammonium hydrosulfite, anhydrous sodium sulfite, diammonium sulfite, dipotassium disulfite, dipotassium pyrosulfite, AMP sulfite, AMP metabisulfite, TEA sulfite, TEA metabisulfite, sodium acid sulfite, sodium hyposulfite, sodium pyrosulfite, and sodium thiosulfate pentahydrate. Details on these inorganic reducing agents are disclosed in WO 2012/027369.

Alternatively, high temperature and alkali-treated keratin, wherein the keratin is heated to around 100° C. or above, dithionites and certain hydrides can be used. Details on these reducing agents are disclosed in U.S. Pat. No. 6,544,499.

K) Tannins

Optionally one or more tannins, specifically gallotannins, ellagitannins, complex tannins, condensed tannins, i.e. tannic acid and its other forms quercitannic acid and gallotannic acid may be used. Tannins represent a class of polyphenol derivatives and are known for their structural diversity. A classification is given based on K. Khanbabaee, T. van Ree, Nat. Prod. Rep., 2001, 18, 641-649 which is herewith included by reference. The most preferred tannin is gallotannic acid (=tannic acid). Preferred tannins include those shown in FIG. 1:

Examples for gallotannins are

R = α, β-OH: 55
R = β-OG: 56

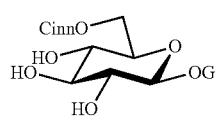

57

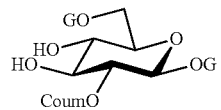

58

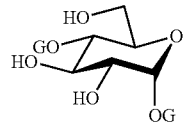

59

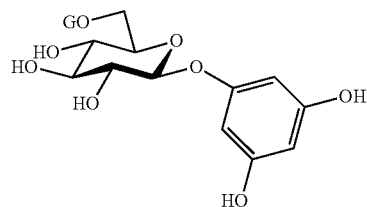

60

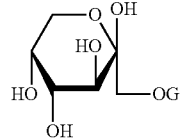

61

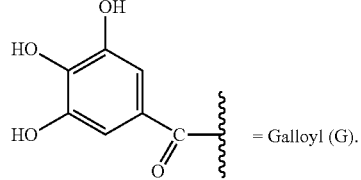

62

= Galloyl (G).

Examples for ellagitannins are

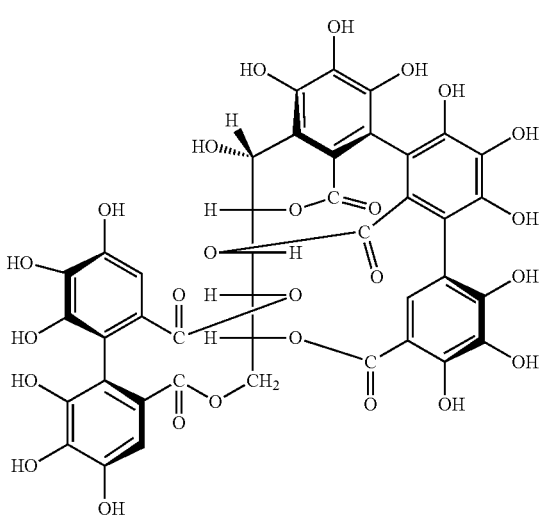

70

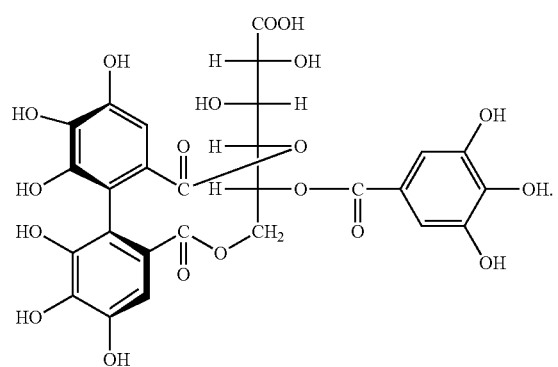
An example for a complex tannin is acutissimin A
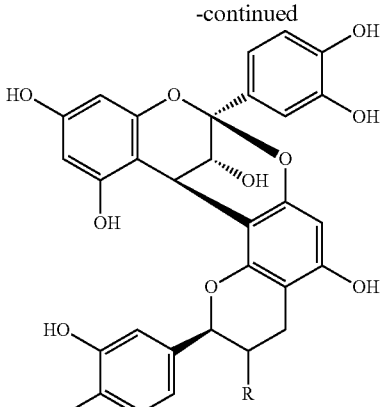
R = ⋯⋯ OH: 78
R = ━ OH: 79
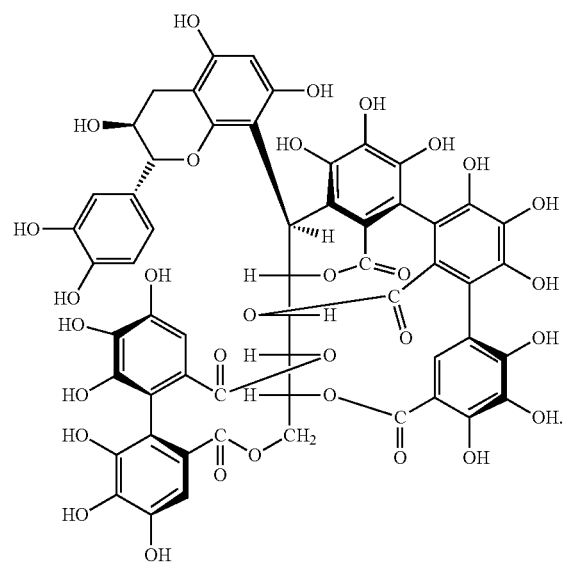
Examples for condensed tannins are procyanidin B2 (77), proanthocyanidin A1 (78), proanthocyanidin A2 (79) and proanthocyanidin C1 (80):
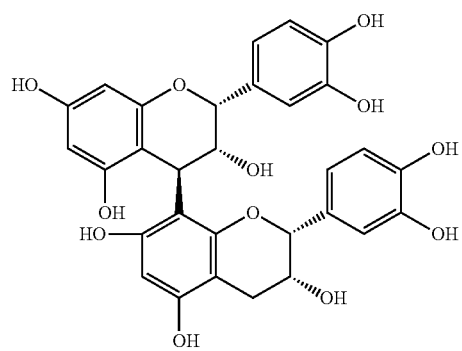
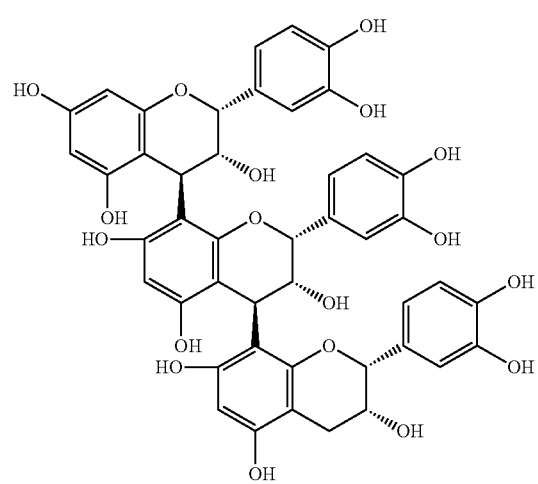
The most preferred tannin is tannic acid:
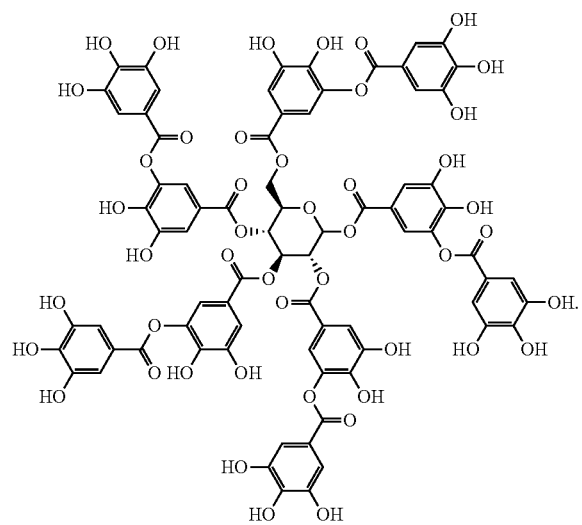 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1]

Metal Salts

Include in particular those of general formula:

$$Me_xA_y$$

wherein Me in this formula is a cation and the number of cations Me is x and the number of anions A is y and the numbers x and y are such that the salt is neutral. x may be e.g. 1 or 2, y may be e.g. 1 to 3 in particular. A is preferably (i) the anion of an oxidized carbohydrate of the formula —O—C(O)—R, or an anion derived from an inorganic or organic acid. Me is preferably an iron or zinc cation.

Particular preferred salts are $Fe^{2+}$ lactobionate, $Fe^{2+}$ maltobionate, $Fe^{2+}$ isomaltobionate, $Fe^{3+}$ lactobionate, $Fe^{3+}$ maltobionate, $Fe^{3+}$ isomaltobionate, $Fe^{2+}$ gluconate, $Fe^{3+}$ gluconate, $Fe^{2+}$ glucoheptonate, $Fe^{3+}$ glucoheptonate, $Fe^{2+}$ glycerophosphate, $Fe^{3+}$ glycerophosphate, $Zn^{2+}$ lactobionate, $Zn^{2+}$ maltobionate, $Zn^{3+}$ isomaltobionate, $Zn^{2+}$ gluconate, and $Zn^{2+}$ glycerophosphate.

Other Auxiliaries

The hair treatment formulations may also comprise one or more additional auxiliaries, i.e. pH adjusting agents, such acids, bases and buffers to adjust the pH value, thickeners (such as polysaccharide thickeners, starch, modified starches, xanthan, gellan, carragenan, pullulan, cellulose, cellulose derivatives, polyacrylic acids, polyacrylates copolymers, polyacrylamides, pectins, clays, fumed silica), lipids, amino acids, sugars, fragrances, sunscreen agents, vitamins, pearlescent agents, gelling agents, trace elements, sequestering agents, antioxidants, humectants, anti-hair loss agents, anti-dandruff agents, propellants, ceramides, polymers, in particular film-forming polymers; fillers, nacres, colorants and in particular pigments and dyes, including hair dyeing agents as described below, all kinds of bioactive phytochemicals, and also mixtures thereof.

Hair Dyeing Agents

Hair dyeing agents include commonly used oxidative or non-oxidative, temporary, semipermanent, demipermanent and permanent hair dyes. Temporary non-oxidative dyes include e.g. Acid Yellow, Acid Orange 7, Acid Yellow 1, Acid Red 33, Acid Red 92, Acid Violet 43, Acid Blue 9, Acid Black 1, which are commonly used in mixtures. Semi-Permanent Non-Oxidative Hair Dyeing Agents contain basic or cationic dyes with low molar mass, and include in particular HC Yellow No. 2, HC Red No. 3, 4-hydroxypropylamino-3-nitrophenol, N,N-bis-(2-hydroxyethyl)-2-nitrophenylenediamine, HC Blue No. 2, Basic Red 51, Basic Red 76, Basic Brown 16, Basic Brown 17, Basic Blue 99, Basic Yellow 57. Other semipermanent dyes, include metallic and vegetables derivatives (such as Henna). The metallic dyes are derived from silver salts, lead, and bismuth. Permanent Oxidative Hair Dyeing Agents include commonly used complex systems of precursors in the presence of an oxidizing agent.

Depending on the polymer structure type and the application purpose certain quantities on acids, bases and/or short chained alcohols are required in order to get transparent formulations. Suitable acids include inorganic or organic acids, like for example carboxylic acids, like acetic acid, hydrochloric acid, sulfuric acid, and phosphoric acid. Suitable bases include aqueous ammonia, alkaline hydroxides, alkaline carbonates, etc.

By adding for example such acids or bases suitable pH ranges of the aqueous compositions can be adjusted such as below 9, preferably below 8.5, preferably below 7.5, more preferably below 7.0.

Preferred precursors for the manufacture of the functionalized polyorganosiloxane A) according to the invention are epoxy modified silicones, preferably based on the well-established addition of allyl glycidyl ether or vinyl cyclohexene oxide to SiH functionalized silicones, i.e. α,ω-propylglycidyl terminated silicones and comb like propylglycidyl substituted silicones, having i.e. the following functional groups (the star indicates where it is bound to the silicon atom)

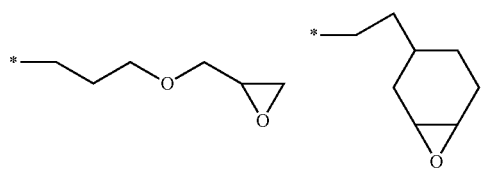

aminofunctionalized silicones, i.e. aminopropyl or aminoethylaminopropyl functionalized silicones which can be synthesized i.e. from the corresponding aminosilanes and silicone precursors containing the desired amount on M, D, T and Q groups by a well-established basic equilibration, i.e. α,ω-aminopropyl or α,ω-aminoethylaminopropyl terminated silicones and comb like aminopropyl or aminoethylaminopropyl substituted silicones, OH terminated polyether modified silicones, i.e. polyethylene oxide modified silicones which can be synthesized in a well-established process from OH terminated allyl polyethers and SiH functionalized silicones, i.e. α,ω-OH terminated polyethyleneoxy propyl silicones and comb like OH terminated polyethyleneoxy propyl substituted silicones.

Functional groups of the formulas

—NH—C(O)—CH=CH—C(O)OH

—NR$^1$—C(O)—CH=CH—C(O)OH can be introduced for example by reacting primary or secondary amino functions containing polyorganosiloxanes with maleic acid anhydride.

Functional groups of the formulas

—O—C(O)—CH=CH—C(O)OH and

—O—C(O)—C(O)H can be introduced in particular by reacting epoxy-functional polyorganosiloxanes with maleic acid and glyoxylic acid.

Functional groups of the formula

—O—C(O)—CH=CH—C(O)OH can be also introduced for example by reacting hydroxyalkylfunctional polyorganosiloxanes with maleic acid anhydride.

Functional groups of the formula

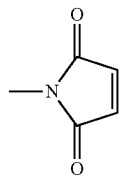

can be introduced for example by reacting primary amino groups containing polyorganosiloxanes with maleic acid anhydride and subsequent dehydration.

Organic Compounds B)

In another embodiment the present invention provides aqueous compositions for the treatment of hair containing at least one organic compound B) having an average number of 2 to 100 carbon atoms selected from the formula:

wherein F is as defined above, and $R^2$ is selected from divalent to octadecavalent hydrocarbon radicals which have up to 100 carbon atoms, and may contain optionally one or more groups selected from —O—, —NH—, —C(O)—, —C(S)—, tertiary amino groups

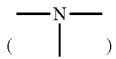

and quaternary ammonium groups

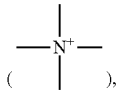

and wherein $R^2$ may optionally be substituted by one or more hydroxyl groups.

The residues $R^2$ have a valency of 2 to 18, preferably 2 to 12, more preferably 2 to 10, and still more preferably 2 to 8, such as 2 to 6.

Optionally such aqueous compositions for the treatment of hair containing at least one organic compound B), comprise at least one surfactant, preferably having a weight ratio of surfactant to organic compound B) of at least 0.06.

In a preferred embodiment of the organic compound B) used in the present invention the molar portion of the carbon atoms in $R^2$ which contain the functional groups F to all carbon atoms is 3.33 to 100 mol %, more preferred 5 to 100 mol %, more preferred 5 to 70 mol %, more preferred 10 to 60 mol %, more preferred 20 to 50 mol %.

The number of carbon atoms in $R^2$ is preferably 2 to 100, preferred 2 to 50, more preferred 2 to 30, even more preferred 2 to 20, even more preferred 2 to 15, specifically 2 to 12, more specifically 3 to 10.

It is within the scope of the invention to use mixtures of different organic compounds B) according to the invention.

It is also within the scope of the invention to use mixtures of polyorganosiloxanes A) and organic compounds B).

The organic radicals $R^2$ are preferably selected from divalent to decavalent, more preferred divalent to hexavalent, even more preferred divalent hydrocarbon radicals which have 2 to 30 carbon atoms, more preferred 2 to 20 carbon atoms, even more preferred 2 to 15 carbon atoms and may contain optionally one or more groups selected from —O—, —NH—, —C(O)—, —C(S)—, tertiary amino groups

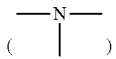

and quaternary ammonium groups

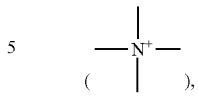

and wherein $R^2$ may optionally be substituted by one or more hydroxyl groups and halogen atoms. Preferably the organic radicals $R^2$ contain at least one ether group (—O—) or polyether group.

In a preferred embodiment the organic compounds B) contain at least one radical $R^2$ selected from:
- C2 to C30 divalent to hexavalent hydrocarbons, preferably derived from di- to hexavalent alcohols, i.e. ethylene glycol, 1,2-propylene glycol, 1,3 propylene glycol, 1,4-butylene glycol, 1,2-hexylene glycol, glycerol, pentaerythrol and sorbitol,
- C2 to C30 divalent to hexavalent polyethers,
  preferably derived from ethylene oxide, propylene oxide and butylene oxide based polyethers, i.e. oligoethylene oxides, like diethylene glycol, triethylene glycol, tetraethylene glycol, pentaethylene glycol, oligopropylene oxides, like dipropylene glycol and tripropylene glycol, mixed ethylene oxide and butylene oxide based copolyethers, mixed propylene oxide and butylene oxide based copolyethers, mixed ethylene oxide and propylene oxide and butylene oxide based copolyethers,
- oligoglycerols, preferably derived from diglycidyl ether and glycerol digylcidyl ether, i.e. diglycerol and triglycerol, and the statistically distributed oligomeric condensation products of glycerol, i.e. diglycerol, triglycerol, tetraglycerol, pentaglycerol, hexaglycerol,
- polyhydroxy alcohol-alkylene oxide addition products, i.e. the addition products of ethylene oxide to glycerol and sorbitol,
- C2 to C30 divalent to hexavalent polyesters, preferably derived from the condensation of di- to hexavalent carboxylic acids, i.e. maleic acid, succinic acid, tartaric acid, trimellitic acid with alkylene oxides, i.e. ethylene oxide, propylene oxide, butylene oxide, glycidol, diglycidyl ether, glycerol diglycidyl ether, i.e. the condensation products of succinic acid, maleic acid and tartaric acid to glycerol diglycidyl ether.

In another preferred embodiment of the invention the hydrocarbons according to the invention contain at least one radical $R^2$ selected from:
an oligoalkylene oxide group of the general formula:

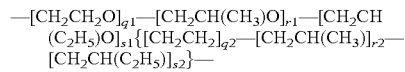

with
q1=0 to 49, preferred 0 to 10, more preferred 1 to 10, even more preferred 1 to 5,
r1=0 to 32, preferred 0 to 10, more preferred 1 to 10, even more preferred 1 to 5,
s1=0 to 24, preferred 0 to 10, more preferred 1 to 10, even more preferred 1 to 5,
q2=0 or 1,
r2=0 or 1,
s2=0 or 1, $$\Sigma(q2+r2+s2)=1,$$

with the proviso that the sum of the carbon atoms is 2 to 100, preferred 2 to 50, more preferred 2 to 30, even more preferred 2 to 20, specific 2 to 15, an oligoglycerol of the general formula:

with
t1=0 to 32, preferred 0 to 10, more preferred 1 to 10, even more preferred 1 to 5, specifically 1 and 2,
t2=1,
$R^5$=OH or F and optionally FA.
with the proviso that the sum of the carbon atoms is 2 to 100, preferred 2 to 50, more preferred 2 to 30, even more preferred 2 to 20, specific 2 to 15, polyesters of the general formulae:

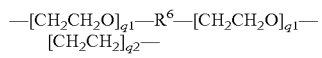

with q1 as defined above and q2=1
and

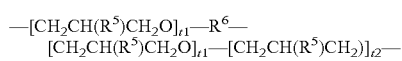

with t1, t2 and $R^5$ as defined above and

i.e. derived from succinic acid,

i.e. derived from phthalic and terephthalic acid,

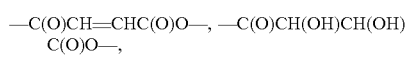

with the proviso that the sum of the carbon atoms is 2 to 100, preferred 2 to 50, more preferred 2 to 30, even more preferred 2 to 20, specific 2 to 15.

Particular preferred organic compounds B) include:

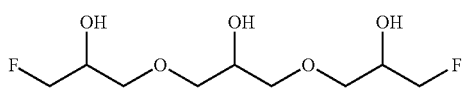 [SMILES: OC(CF)COCC(O)COCC(O)CF]

with F being as defined above, preferably F being —O—C(O)—C(O)H,

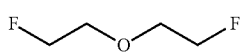

with F being as defined above, preferably F being —O—C(O)—CH=CH—C(O)OH,

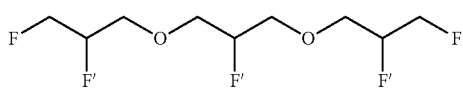

with F being as defined above, preferably F being —O—C(O)—CH=CH—C(O)OH, and F' being hydroxyl or F, preferably F being —O—C(O)—CH=CH—C(O)OH.

Particular preferred organic compounds B) include commercially available bis-maleimides of the formulae (such as those delivered from thermos scientific):

BMOE, bis(maleimido)ethane:

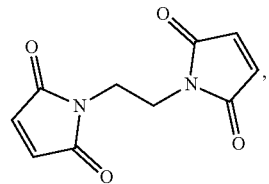 [SMILES: O=C1C=CC(=O)N1CCN1C(=O)C=CC1=O]

BMB 1,4-bis(maleimido)butane:

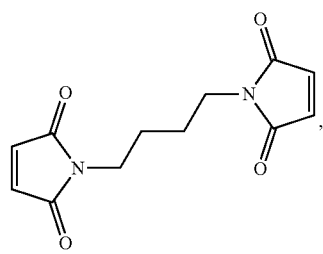 [SMILES: O=C1C=CC(=O)N1CCCCN1C(=O)C=CC1=O]

BMH, bis(maleimido)hexane:

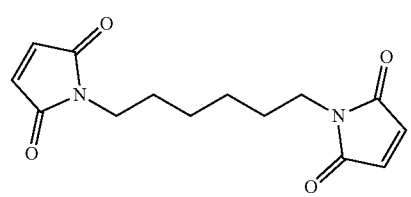 [SMILES: O=C1C=CC(=O)N1CCCCCCN1C(=O)C=CC1=O]

bis (maleimido) polyethylene glycol:

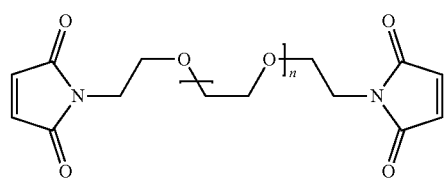

wherein n in this formula is ≥1, preferably 1 or 2.

The optional at least one surfactant used in combination with the organic compound B) is preferably selected from hydrocarbon based or silicone based emulsifiers having a HLB value ranging from 1 to 20, preferred 7 to 20, more preferred 8 to 20.

The weight ratio of the surfactant to organic compound B) of the formula:

is at least 0.06, preferred 0.06 to 5, more preferred 0.06 to 3, even more preferred 0.1 to 3, specifically 0.1 to 1.

Depending on the chemical nature of the continuous and discontinuous phase emulsifiers having a HLB value <7 (W/O emulsion type) or >7 (O/W emulsion type) are preferably selected.

In a preferred embodiment of the invention the aqueous hair treatment composition comprising the organic compound B) is a W/O formulation. In another preferred embodiment of the invention the aqueous hair treatment composition comprising the organic compound B) is an O/W formulation.

Preferred examples for hydrocarbon based emulsifiers are cationic, non-ionic, betaine and anionic emulsifiers. Details on specifically preferred hydrocarbon based emulsifiers were outlined above for the polyorganosiloxane component A). The compositions of the present invention preferably comprise the hydrocarbon based cationic, nonionic, betaine and anionic surfactants in an amount of from about 0.05% to about 15%, preferably from about 0.05% to about 5%, still more preferably from about 0.1% to about 5%, specifically from 0.1 to 3% by the total weight of the aqueous composition.

Preferred examples for silicone based emulsifiers are cationic, nonionic, betaine and anionic emulsifiers.

Details on specifically preferred silicone based emulsifiers and their preferred amounts were outlined above for the polyorganosiloxane A).

Details of the possible additives for the aqueous compositions comprising the organic compound B) are outlined above.

In a preferred embodiment of the invention the aqueous hair treatment compositions comprise the organic compound B) in a concentration range from 0.05 to 30%, preferred 0.5 to 30%, more preferred 1 to 30%, even more preferred 1 to 20%, specifically 1 to 10%, wherein each percentage is per weight based on the total weight of the composition.

The above described aqueous compositions according to the invention are particularly useful for strengthening of hair, for hair color retention, for hair color enhancement, for hair color protection, for shaping of hair, i.e. the curling and straightening of hair, for hair conditioning, for hair smoothening or softening, for hair straightening, for improving manageability of the hair, in particular for improving the combability of the hair. They can provide in particular benefits with respect to an improved durability of artificial colors on hair, and have additionally a hair strengthening and shaping effect as well as a conditioning effect.

The aqueous compositions according to the invention can be formulated into a form typical for hair treatment compositions. Preferred are topical hair care or treatment compositions, e.g. hair tonics, conditioners, hair-care preparations, e.g. pre-treatment preparations, styling creams, styling gels, pomades, hair rinses, treatment packs, intensive hair treatments e. g. leave-on and rinse-off deep conditioners, hair-structuring preparations, e.g. hair-waving preparations for permanent waves (hot wave, mild wave, cold wave), hair-straightening preparations, liquid hair-setting preparations, hair foams, hair serums, hair sprays, bleaching preparations, e g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile. Based on the application the hair care preparations may be in particular in the form of a (aerosol) spray, (aerosol) foam, gel, gel spray, cream, lotion, liquid, serum or a wax, mousse, shampoo, such as pearl shampoo, anti-frizz shampoo etc.

EXAMPLES (The percentages refer to weight-% unless otherwise indicated).

Example 1

A Silicone Glyoxylic Acid Ester Derivative (Terminal)

In a 100 ml three-necked flask, equipped with refluxing condenser, thermometer and magnetic stirrer, 17.35 g (17.7 mmol epoxy groups) of a silicone diepoxide of the structure

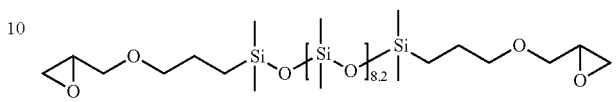

3.28 g (35.6 mmol) glyoxylic acid, 0.4 g trimethylamine and 48 g methoxypropyl acetate are mixed at room temperature und $N_2$. The mixture is heated to 80° C. for 20 hours. Afterwards, the mixture is cooled to room temperature and the conversion of the epoxide groups determined by means of $^1H$ NMR spectroscopy. The conversion of epoxy groups is 96%.

A product essentially consisting of the following structure is obtained

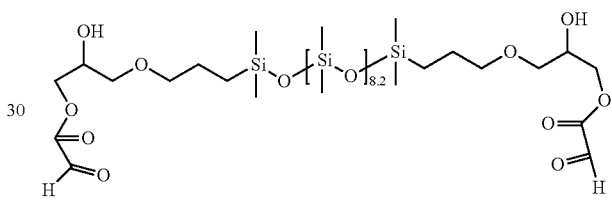

Example 2

A Glycerol Diglycidyl Ether Based Glyoxylic Acid Ester Derivative

In a 100 ml three-necked flask, equipped with refluxing condenser, thermometer and magnetic stirrer, 10 g (97.9 mmol epoxy groups) of glycerol diglycidylether, 22 g t-butanol and 0.38 g trimethylamine are mixed and heated to 80° C. Separately, 9 g (97.9 mmol) glyoxylic acid are mixed with 22 g t-butanol and heated to 35° C. This warm liquid mixture is added slowly to the glycerol diglycidyl ether solution. The mixture is kept at 80° C. for 10 hours. Afterwards, the mixture is cooled to room temperature and the conversion of the epoxide groups determined by means of $^1H$ NMR spectroscopy. The conversion of epoxy groups is 98%.

A product essentially consisting of the following structure is obtained

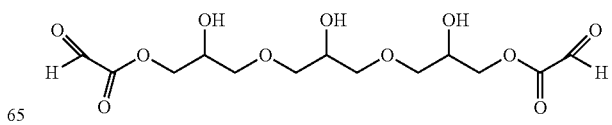

Example 3

A Silicone Maleic Acid Ester Derivative in Different Solvents

Example 3a

In a 250 ml three-necked flask, equipped with refluxing condenser, thermometer and magnetic stirrer, 15.3 g (40 mmol epoxy groups) of a silicone diepoxide of the structure

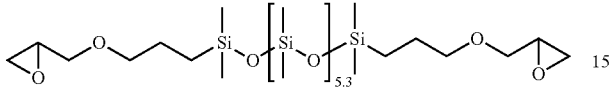

4.7 g (80 mmol COOH groups) maleic acid, 0.6 g trimethylamine and 46.6 g methoxypropyl acetate are mixed at room temperature under $N_2$. The mixture is heated to 80° C. for 25 hours. Afterwards, the homogeneous mixture is cooled to room temperature and the conversion of the epoxide groups determined by means of $^1$H NMR spectroscopy. The conversion of epoxy groups is 100%.

Example 3b

In a 100 ml three-necked flask, equipped with refluxing condenser, thermometer and magnetic stirrer, 7.65 g (20 mmol epoxy groups) of a silicone diepoxide of the structure

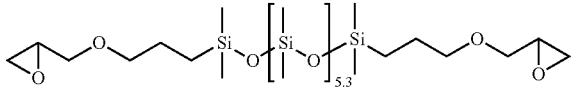

2.5 g (40 mmol COOH groups) maleic acid, 0.3 g trimethylamine and 23.3 g dipropylene glycol are mixed at room temperature under $N_2$. The mixture is heated to 80° C. for 14 hours. Afterwards, the homogeneous mixture is cooled to room temperature and the conversion of the epoxide groups determined by means of $^1$H NMR spectroscopy. The conversion of epoxy groups is 97.7%.

Example 3c

In a 100 ml three-necked flask, equipped with refluxing condenser, thermometer and magnetic stirrer, 7.65 g (20 mmol epoxy groups) of a silicone diepoxide of the structure

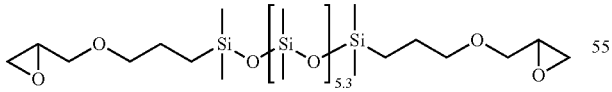

2.35 g (40 mmol COOH groups) maleic acid, 0.3 g trimethylamine and 23.3 g 1,3-butane diol glycol are mixed at room temperature under $N_2$. The mixture is heated to 80° C. for 14 hours. Afterwards, the two phase mixture is cooled to room temperature and the conversion of the epoxide groups determined by means of $^1$H NMR spectroscopy. The conversion of epoxy groups is 97.5%.

A product essentially consisting of the following structure is obtained in Examples 3a, 3b and 3c:

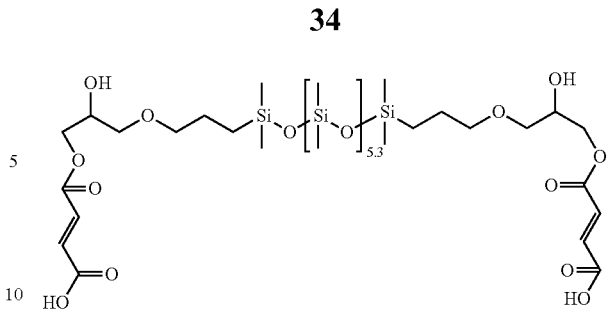

Example 4

A Diethylene Glycol Based Maleic Acid Ester Derivative

In a 250 ml three-necked flask, equipped with refluxing condenser, thermometer and magnetic stirrer, 10.6 g (200 mmol OH groups) of diethylene glycol, 19.6 g maleic anhydride (200 mmol anhydride groups) and 0.3 g trimethylamine are dissolved in 70 g methoxypropyl acetate. The mixture is heated to 61° C. for 12 h. Afterwards, the mixture is cooled to room temperature and the conversion of the anhydride determined by means of $^1$H NMR spectroscopy. The conversion of anhydride groups is 100%.

A product essentially consisting of the following structure is obtained

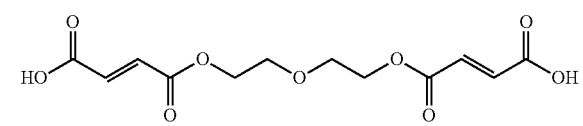 [SMILES: O=C(O)/C=C/C(=O)OCCOCCOC(=O)/C=C/C(=O)O]

Example 5

Synthesis of a Glyoxylic Acid Derivative (Comb Like)

104.2 g propylene glycol mono methyl ether, 8.28 g (0.0901 mol —COOH) glyoxylic acid monohydrate, 0.86 g triethylamine and 38.7 g (0.0901 mol epoxy groups) of an epoxy functionalized silicone of the structure

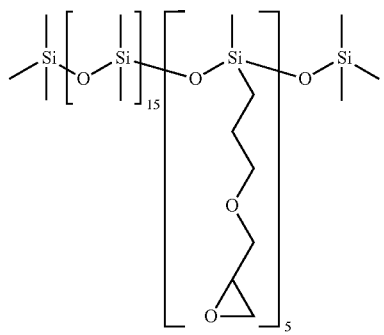

were mixed at room temperature and heated to 100° C. for 33 hrs. The conversion of epoxy groups was 96% ($^1$H-NMR).

A transparent yellow to slightly brownish polymer solution was obtained (Example 5). The polymer has the approximate structure

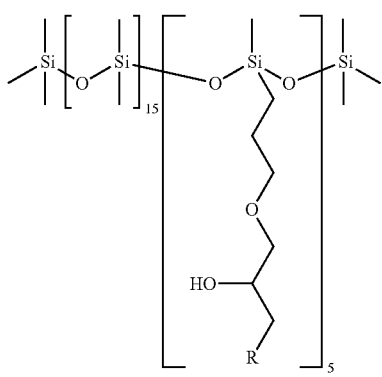

with

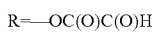

was obtained.

Example 6

Glycerol Diglycidylether with Three Maleic Ester Functions

In a 250 ml three-necked flask, equipped with refluxing condenser, thermometer and magnetic stirrer, 10 g (97.9 mmol epoxy groups) of glycerol diglycidylether, 11.36 g maleic acid (97.9 mmol), 61 g methoxypropyl acetate and 0.52 g trimethylamine are mixed and heated to 80° C. for 6 hrs. The conversion of the epoxide groups, as determined by means of $^1$H NMR spectroscopy is 100%. 4.79 g (48.9 mmol) maleic acid anhydride are added and the reaction continued at 80° C. for 10 hrs. The conversion of the anhydride groups, as determined by means of $^1$H NMR spectroscopy, is 100%.

A product essentially consisting of the following structure (example 6) is obtained

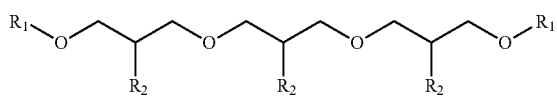

with
$R_1$—C(O)CH=CHCOOH
$R_2$—OH and —OC(O)CH=CHCOOH in the ratio of 2:1

Example 7

A Polyether Siloxane with Maleic Ester Functions

In a 250 ml three-necked flask, equipped with refluxing condenser, thermometer and magnetic stirrer, 21.08 g (48.9 mmol OH groups) of a polyethersiloxane of the structure

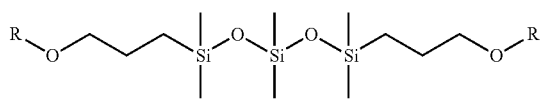

with

4.79 g maleic anhydride (48.9 mmol anhydride groups) and 0.51 g trimethylamine are dissolved in 60.4 g methoxypropyl acetate. The mixture is heated to 80° C. for 11 hrs. Afterwards, the yellowish mixture is cooled to room temperature and the conversion of the anhydride determined by means of NMR spectroscopy. Conversion anhydride groups 97%.

A product essentially consisting of the following structure (example 7) is obtained

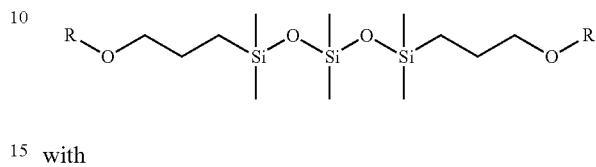

with

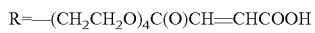

Example 8

Synthesis of a Difunctional Trihydroxy Benzoic Acid and Glyoxylic Acid Derivative 58.63 g propylene glycol mono methyl ether, 4.60 g (0.027 mol —COOH) 3,4,5-trihydroxy benzoic acid, 1.65 g (0.018 mol —COOH) glyoxylic acid monohydrate, 0.5 g triethylamine and 19.35 g (0.045 mol epoxy groups) of an epoxy functionalized silicone of the structure

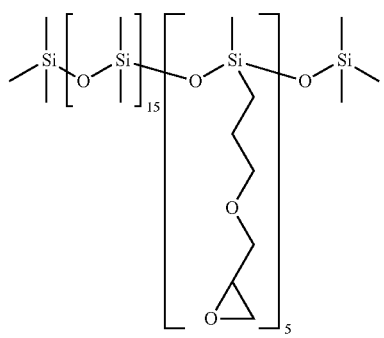

were mixed at room temperature and heated to 100° C. for 55 hrs. The conversion of epoxy groups was 96% ($^1$H-NMR).

A transparent brownish polymer solution was obtained (Example 8). The polymer has the approximate structure

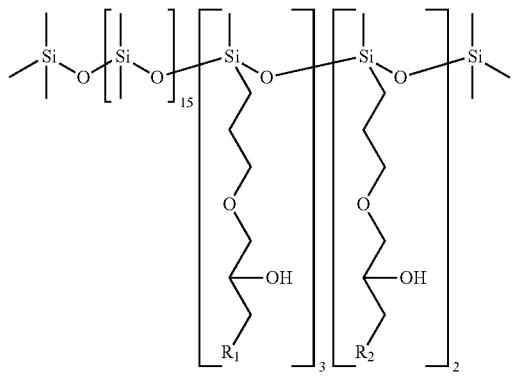

with
$R_1=$

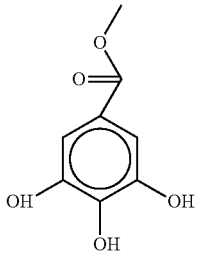

and $R_2=$—OC(O)C(O)H
was obtained.

Application Tests

Test Method

Test method for evaluation of the color retention is described in detail in US 2011/0219552 A1. The method determines the hair color changes before and after washes by Delta E. Color changes were measured by measuring Hunter L, a and b values on a HunterLab colorimeter.

The meaning of L, a, b was elaborated in "Practical Modern Hair Science" Trefor Evans and R. Randall Wichett, Alluredbooks, Carol Stream, Ill., 2012. The L value measures the lightness from L=0 (black) to L=100 (white). The color is measured by a from negative value (green) to positive value (red) and b from negative value (blue) to positive value (yellow). For example, a medium blonde has an L, a, b value of L=49, a=12, b=26 and a medium auburn has an L, a, b value of L=26, a=13, b=12.

Delta E was calculated using the following equation to evaluate color change before and after washes.

$$\text{Delta } E = ((L_t - L_0)^2 + (a_t - a_0)^2 + (b_t - b_0)^2)^{1/2}$$

Where $L_0$, $a_0$, $b_0$, and $L_t$, $a_t$, $b_t$ are measured Hunter L, a, b color parameters before and after washing, respectively.

The larger value of Delta E reflects greater change of color, so smaller Delta E is desired because it indicates less color loss after washing.

Similarly, color enhancement was calculated using the following equation to evaluate initial color depth increase with treatment.

$$\text{Delta } E = ((L_2 - L_1)^2 + (a_2 - a_1)^2 + (b_2 - b_1)_2)^{1/2}$$

Where $L_2$, $a_2$, $b_2$, and $L_1$, $a_1$, $b_1$ are measured Hunter L, a, b before washing color parameters with and without treatment respectively. Here larger Delta E is desired because it means more initial color enhancement.

Example 9

Example 9.1 Application on Color Enhancement and Color Retention of Platinum Bleached Hair The following treatment solution TS1, TS2, TS3 and TS4 were prepared:

TS1 solution (silicone based maleic ester from example 3a) approximately 50 ml was composed of the polyorganosiloxane A) from example 3a (the silicone maleic ester) 3 g, 7 g methoxypropyl acetate (that is 10 g of the solution of the polyorganosiloxane in methoxypropyl acetate obtained in example 3a are used), 27.5 ml isopropyl alcohol and 12.5 g water.

TS2 solution (organic maleic ester from example 4) approximately 50 ml was composed of the organic compound B) from example 4 (the organic maleic ester) 3 g, 7 g methoxypropyl acetate (that is 10 g of the solution of the organic compound B) in methoxypropyl acetate obtained in example 4 are used) and 40 g water.

TS3 solution (silicone based glyoxylic ester from example 1) approximately 50 ml was composed of the polyorganosiloxane A) from example 1 (the silicone glyoxylic ester) 3 g, 7 g methoxypropyl acetate (that is 10 g of the solution of the polyorganosiloxane in methoxypropyl acetate obtained in example 1 are used), 32.5 g isopropyl alcohol and 7.5 g water.

TS4 solution (organic glyoxylic ester from example 2) approximately 50 ml composed of the organic compound B) from example 2 (the organic glyoxylic ester) 3 g, 7 g methoxypropyl acetate (that is 10 g of the solution of the organic compound B) in methoxypropyl acetate obtained in example 2 are used), 8 g isopropyl alcohol and 32 g water.

The hair dye was a commercial hair dye Feria 66 very rich auburn from L'Oreal.

Pre-Treatment According to Invention

A bundle of 4 g platinum bleached hair tress (International Hair Importers) was immersed in 10 g TS1 or TS2 or TS3 or TS4 solution for 30 minutes. Then the hair was dried at room temperature overnight. The hair bundle was then washed by 10 wt-% SLES (Sodium Lauryl Ether Sulfate) for 3 times. Hair was dried and then dyed with Feria 66 dye for 25 minutes following the standard dyeing procedure of Feria 66.

The control tress was the tress treated by 50 ml water. And then washed with 10 wt-% SLES and dyed with Feria 66 dye same as hair tress treated by crosslinking technology. The initial color was measured.

Wash Protocol

The Dyed tresses were immersed in 450 ml of a 2.5 wt-% SLES solution at 41° C. The solution with the tress was stirred with a magnetic stirrer for 5 minutes at 400 rpm. After 5 minutes, the hair was dried and the hair color was measured.

Color Enhancement Delta E

| | Initial Color L, a, b | | | Color Enhancement |
|---|---|---|---|---|
| | L | A | b | Delta E |
| Control | 24.33 | 15.42 | 8.27 | |
| TS1 (maleic silicone expl. 3) | 18.85 | 9.12 | 3.09 | 9.826128 |
| TS2 (maleic organic expl. 4) | 17.11 | 7.36 | 2.29 | 10.18585 |
| TS3 (glyoxylic silicone expl. 1) | 18.91 | 10.15 | 3.49 | 7.339026 |
| TS4 (glyoxylic organic expl. 2) | 21.23 | 11.71 | 5.94 | 4.957358 |

The technology according to the invention shows a color enhancement effect with darker initial color compared to the control.

| | Color Loss Delta E |
|---|---|
| Control | 10.62 |
| TS1 (maleic silicone expl. 3) | 7.23 |
| TS2 (maleic organic expl. 4) | 7.52 |
| TS3 (glyoxylic silicone expl. 1) | 7.95 |
| TS4 (glyoxylic organic expl. 2) | 7.45 |

The technology according to the invention shows a color retention effect with lower color loss Delta E.

Example 9.2: Bleaching Treatment

Undamaged Dark brown hair tresses were obtained from Hair International Importers. A commercial bleaching lightener powder (9 grams) and a commercial 40 volume developer (aqueous 12 wt-% hydrogen peroxide) (11 grams) were mixed together. 1 gram of a 30% solution of the organic maleic ester derivative of example 4 in methoxypropyl acetate was added to the bleach mixture and stirred manually until uniform. The bleaching composition was applied to the virgin dark brown hair tress, spread through and left on the hair tress for 50 min. After rinsing the dye from the tress with tap water, the tress was washed with a 10 wt-% Sodium Laureth Sulfate (2 EO) solution and rinsed. Comparative tress 1 was the untreated tress. Comparative tress 2 was a tress treated with the bleached mixture without the polymer of the invention.

Results:

The Example tress 2 felt much smoother than the comparative tress 2. 50 fibers from the comparative tresses and the example tress were subjected to a continuous strain and analyzed by a Diastron automated tensile tester. The example tress 2 had stronger tensile properties than the comparative control tress 2.

|  | Young Modulus (Pa) | Break strength (gm/μm$^2$) |
| --- | --- | --- |
| Comparative tress 1 | $1.90 \cdot 10^9$ | $1.95 \cdot 10^{-2}$ |
| Comparative tress 2 | $1.70 \cdot 10^9$ | $1.84 \cdot 10^{-2}$ |
| Example Tress 2 | $1.76 \cdot 10^9$ | $1.88 \cdot 10^{-2}$ |

Example 9.3: Bleaching Treatment

Undamaged Dark brown hair tresses were obtained from Hair International Importers. A commercial bleaching lightener powder (9 grams) and a commercial 40 volume developer (11 grams) were mixed together. 1 gram of a 30 wt-% solution of the siloxane based maleic ester derivative of example 3 in methoxypropyl acetate was added to the bleach mixture and stirred manually until uniform. The bleaching composition was applied to the virgin dark brown hair tress, spread through and left on the hair tress for 50 min. After rinsing the dye from the tress with tap water, the tress was washed with a 10 wt % Sodium Laureth Sulfate (2 EO) solution and rinsed. Comparative tress 1 was the untreated tress. Comparative tress 2 was a tress treated with the bleached mixture without the polymer of the invention.

Results:

The Example tress 3 felt much smoother than the comparative tress 2. 50 fibers from the comparative tresses and the example tress were subjected to a continuous strain and analyzed by a Diastron automated tensile tester. The example tress 3 had stronger tensile properties than the comparative control tress 2.

|  | Young Modulus (Pa) | Break strength (gm/μm$^2$) |
| --- | --- | --- |
| Comparative tress 1 | $1.90 \cdot 10^9$ | $1.95 \cdot 10^{-2}$ |
| Comparative tress 2 | $1.70 \cdot 10^9$ | $1.84 \cdot 10^{-2}$ |
| Example Tress 3 | $1.74 \cdot 10^9$ | $1.87 \cdot 10^{-2}$ |

Example 9.4: White Rinse Off Conditioner Formulation

|  | Chemical Name | wt % |
| --- | --- | --- |
| A | Water | q.s. to 100 |
| B | Lactic Acid | 0.6 |
|  | Amidet APA-22 (Behenamidopropyl Dimethylamine) from Kao Corporation | 2.2 |
| C | Kalcol 6850 (Cetostearyl alcohol) from Kao Corporation | 4.4 |
| D | maleic silicone as in example 3a | 5 |

1. Part A. Lactic acid and water were mixed and heated to 80° C.
2. Part B was added to part A and the mixture stirred for 1-3 hours at 80° C. to provide a homogeneous formulation.
3. Part C was added to the mixture of A and B and stirred at 80° C. for 0.5 to 1 hour until Part C was completely molten and a homogeneous mixture was obtained.
4. The heating source was removed while stirring continued until room temperature was reached.
5. Part D was added to the mixture consisting of A+B+C and stirring continued until a homogeneous mixture was reached.

Example 9.5. Pearlescent Shampoo Formulation

|  | Component | wt % |
| --- | --- | --- |
| A | Sodium Laureth Sulfate | 12 |
|  | Cocamidopropyl Betaine | 3 |
| B | Ethylene Glycol Distearate | 1 |
|  | Water | 10 |
| C | Cocamide Monoethanolamine | 1 |
|  | Water | 10 |
| D | Polyquaternium-6 | 0.06 |
|  | ACULYN™ 38 from the Dow Chemical Company (10 wt-% active) | 3 |
| E | maleic silicone expl. 3a MPA solution | 5 |
| F | Water | q.s. to 100 |

Part A: The components of part A were mixed with an overhead mechanical stirrer at 600 rpm for 10 minutes.

Part B: 1 g ethylene glycol distearate and 10 g water were mixed with a magnetic stirrer at 200 rpm for 15 minutes.

Part C: 1 g cocamide monoethanolamine and 10 g water were mixed with a magnetic stirrer at 200 rpm for 15 minutes.

The components of part D were added to part A and stirred with an overhead mechanical stirrer at 600 rpm for 10 minutes. A mixture A+D was obtained.

Part B was added to the mixture A+D and stirred for 10 minutes at 600 rpm with a mechanical stirrer. Mixture A+D+B was obtained.

Part C was added to the mixture A+D+B and stirred for 10 minutes at 600 rpm with a mechanical stirrer. Mixture A+D+B+C was obtained.

Part E was added to the mixture A+D+B+C and stirred for 15 minutes at 600 rpm with a mechanical stirrer. Mixture A+D+B+C+E was obtained.

Part F was added last to the mixture A+D+B+C+E and the mixture stirred for 15 minutes at 600 rpm with a mechanical stirrer.

Example 9.6: Pearlescent Shampoo Non-Sulfate Version

|   | Component | Wt % |
|---|---|---|
| A | Sodium Lauryl Sulfoacetate + Disodium Laureth Sulfosuccinate | 10.6 |
|   | Cetyl Betaine | 3.3 |
| B | Cocamide Monoethanolamide | 1.5 |
|   | Water | 10 |
| C | Hydroxypropyl Methylcellulose | 1.5 |
|   | Water | 10 |
| D | Ethylene Glycol Distearate | 1.5 |
|   | Water | 10 |
| E | Polyquaternium-10 | 0.15 |
| F | maleic silicone in MPA from expl. 3a | 5 |
| G | Water | q.s. to 100 |

Part A: The components of part A were mixed with an overhead mechanical stirrer at 600 rpm for 10 minutes.

Part B: 1.5 g cocamide monoethanolamide was mixed with 10 g water (45° C.) with a magnetic stirrer at 200 rpm for 30 minutes.

Part C: 1.5 g hydroxypropyl methylcellulose powder was slowly added to 10 g water (45° C.) and stirred with a magnetic stirrer at 200 rpm for 30 minutes.

Part D: 1.5 g ethylene glycol distearate powder was slowly added to 10 g water (45° C.) and stirred with a magnetic stirrer at 200 rpm for 30 minutes.

Part B was slowly added to part A with mechanical stirring at 600 rpm for 5 minutes. Mixture A+B was obtained.

Part C was slowly added to part A+B with mechanical stirring at 600 rpm for 5 minutes. Mixture A+B+C was obtained.

Part D was slowly added to part A+B+C with mechanical stirring at 600 rpm for 5 minutes. Mixture A+B+C+D was obtained.

Part E was added to part A+B+C+D with mechanical stirring at 600 rpm for 10 minutes. Mixture A+B+C+D+E was obtained.

Part F was added to the mixture A+B+C+D+E and mechanically stirred for 15 minutes at 600 rpm.

Finally, Part G was added and the mixture stirred at 600 rpm for 30 minutes.

Example 9.7: Anti-Frizz Shampoo

|   | Component | wt % |
|---|---|---|
| A | Water | 55 |
|   | PEG-120 Methyl Glucose Dioleate | 2 |
| B | Water | 15.25 |
|   | Sodium Laureth Sulfate | 9 |
| C | Dissodium EDTA | 0.1 |
|   | Cocamidopropyl Betaine | 10 |
|   | Polyquaternium-7 | 0.5 |
|   | Decyl Glucoside | 1 |
|   | Dexpanthenol | 1 |
|   | Phenoxyethanol | 0.5 |
| D | maleic silicone in MPA as expl. 3a | 5 |
|   | Tropicalism 18 from Givaudan S.A. | 0.65 |

Part A: The components of part A were mixed with a magnetic stirrer at 200 rpm for 15 minutes.

Part B: The components of part B were mixed with a magnetic stirrer at 200 rpm for 15 minutes.

Part B was added to part A and the mixture stirred with an overhead mechanical stirrer at 500 rpm for 15 minutes.

The Components of part C were added to the mixture A+B and stirred with an overhead mechanical stirrer at 500 rpm for 1 hour.

The components of part D were mixed with a magnetic stirrer at 200 rpm for 15 minutes and afterwards added to the mixture A+B+C.

Finally, the complete mixture A+B+C+D was mixed with a mechanical stirrer at 500 rpm for 30 minutes.

Example 9.8: Water Based Spray Formulation 1.5 wt % Maleic silicone expl. 3
3.5 wt % MPA,
1.25 wt % SLES,
0.09 wt % NaOH (added as a 10 wt % active NaOH solution in water of pH 8)
Water q.s. to 100 wt %

Example 9.9: Isopropanol (IPA) Based Spray Formulation 1.5 wt % Maleic silicone expl. 3
3.5 wt % MPA
IPA q.s. to 100%

Example 10: Treatment Gel and Cream Formulations

Example 10.1

| | Formulation | | | | |
|---|---|---|---|---|---|
| Ingredients | 1 Wt % | 2 wt | 3 Wt % | 4 Wt % | 5 Wt % |
| Carbopol 1382 | 1 | 1 | | | |
| Xanthan gum | 0.1 | 0.1 | 0.5 | | |
| Hydroxypropyl starch phosphate | | | | 4 | |
| Hydroxyethyl cellulose | | | | | 1 |
| Maleic silicone in MPA as in example 3a, b or c | 10 | | 10 | | 5 |

-continued

| Ingredients | Formulation 1 Wt % | 2 wt | 3 Wt % | 4 Wt % | 5 Wt % |
|---|---|---|---|---|---|
| Maleic organic as in example 4 | | 10 | | 10 | |
| Dipropylene glycol | 30 | | | | |
| Butylene glycol | | | 30 | | 30 |
| isopropanol | 25 | | 25 | | 25 |
| water | q.s 100 | q.s 100 | q.s 100 | q.s 100 | q.s 100 |
| NaOH 10% | q.s pH 7 | q.s pH 7 | q.s pH 6.5 | q.s pH 6.5 | q.s pH 6.5 |

Example 10.2

| Ingredients | Wt % |
|---|---|
| Phospholipids (and) glycine soja oil | 2 |
| propanediol | 3 |
| Maleic acid ester derivative as in example 4 | 10 |
| Sodium acrylates copolymer and lecithin | 1.7 |
| Stearic acid | 0.5 |
| Behenyl alcohol | 0.5 |
| Isononyl isononaote | 2 |
| Glycerin and picea abies extract and alcohol | 1 |
| phenoxyethanol | 0.5 |
| Butylene glycol dicaprylate/dicaprate | 2 |
| water | q.s to 100 |

The invention claimed is:

1. An aqueous composition for hair treatment, comprising at least one polyorganosiloxane A) having an average number of 2 to 1000 siloxy units selected from the siloxy groups of the formulas:

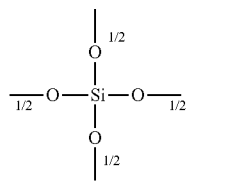

(Q)

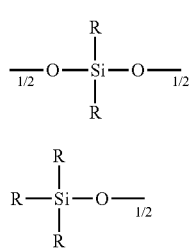

(D)

(M)

wherein
each R is independently selected from $R^1$ and $R^F$, wherein $R^1$ is selected from organic groups bound to the silicon atoms by a carbon atom, and two groups $R^1$ may form a bridging group between two silicon atoms, and $R^F$ is selected from organic groups different from $R^1$ and is bound to the silicon atoms by a carbon atom, which contain at least one functional group F which is defined as:

with the proviso that the at least one polyorganosiloxane A) comprises at least one $R^F$ group and the least one polyorganosiloxane A) does not comprise siloxy units

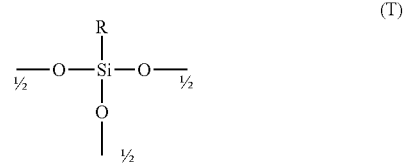

(T)

and/or at least one organic compound B) selected from the formula:

$R^2$—(F)$_{2-18}$ wherein F is as defined above, and
$R^2$ is selected from hydrocarbon radicals having a valency of 2 to 18, which have up to 100 carbon atoms, and may optionally contain one or more groups selected from —O—, —NH—, —C(O)—, —C(S)—, tertiary amino groups

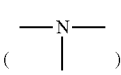

and quaternary ammonium groups

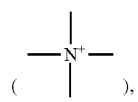

and wherein $R^2$ is substituted by one or more groups selected from hydroxyl groups and halogen atoms, and wherein the composition further comprises at least one surfactant, wherein the weight ratio of said surfactant to the polyorganosiloxane A) or the compound B) is from 0.06 to 5.

2. The aqueous composition according to claim 1, wherein the polyorganosiloxane A) comprises at least two groups $R^F$.

3. The aqueous composition according to claim 1, comprising from 0.1 to 20 wt-% of the polyorganosiloxane A) or the compound B) based on the weight of the aqueous composition.

4. The aqueous composition according to claim 1, wherein in the at least one polyorganosiloxane A), $R^F$ is a group of the formula

wherein F is as defined above and $R^3$ is selected from a divalent hydrocarbon radical which has up to 30 carbon atoms, which optionally contains one or more groups selected from —O—, —NH—, —C(O)—, —C(S)—, tertiary amino groups

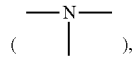

and quaternary ammonium groups

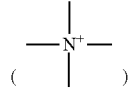

and wherein $R^3$ optionally is substituted by one or more hydroxyl groups.

5. The aqueous composition according to claim 1, wherein in the at least one polyorganosiloxane A) the molar ratio of the siloxanyl units which contain the group $R^F$ to all siloxanyl units of the polyorganosiloxane A) is 3.33 to 100 mol %.

6. The aqueous composition according to claim 1, wherein in the at least one polyorganosiloxane A) the molar ratio of branching Q moieties is 0 to 50% based on all siloxy units.

7. The aqueous composition according to claim 1, wherein the average number of siloxy units in the at least one polyorganosiloxane A) is 2 to 300.

8. The aqueous composition according to claim 1, wherein the organic radicals $R^1$ are selected from the group consisting of straight-chain, cyclic or branched, saturated, unsaturated or aromatic hydrocarbon radicals which have up to 100 carbon atoms which optionally contain one or more groups selected from —O—, —NH—, —C(O)—, —C(S)—, tertiary amino groups

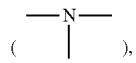

and quaternary ammonium groups

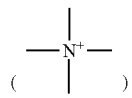

and which are optionally substituted by one more groups selected from the group consisting of hydroxyl, halogen, a polyether radical with up to 60 carbon atoms, or two radicals $R^1$ from different siloxy moieties form a straight-chain, cyclic or branched, saturated, unsaturated or aromatic alkandiyl hydrocarbon radical which 2 to 20 carbon atoms between two silicon atoms, which are optionally substituted by one or more hydroxyl groups and/or halogen atoms, and are linked to silicon by a carbon atom, and wherein
$R^F$ is a group of the formula
—$R^3$—F, wherein $R^3$ is selected from divalent saturated hydrocarbon radicals with up to 20 carbon atoms, optionally containing one or two —O— groups, which may be substituted by hydroxyl, and F is as defined above.

9. The aqueous composition according to claim 1, wherein the at least one polyorganosiloxane A) contains at least two radicals of the formula $M^F$ and/or $D^F$:

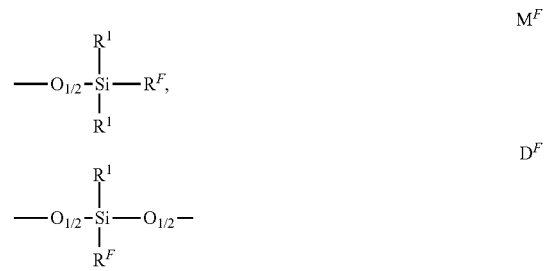

wherein $R^1$ and $R^F$ are as defined above.

10. The aqueous composition according to claim 1, wherein the at least one polyorganosiloxane A) is selected from the formulas:

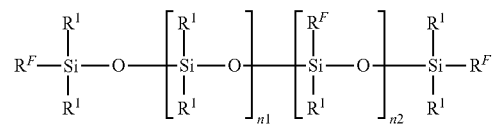

wherein $R^1$ and $R^F$ are as defined above, and n1+n2 is 0 to 28,

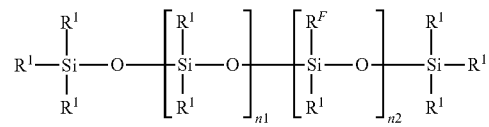

wherein $R^1$ and $R^F$ are as defined above, n1+n2 is 2 to 28, with n2≥1, and

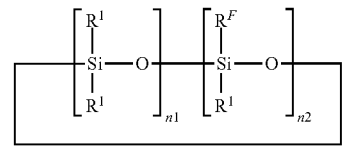

wherein $R^1$ and $R^F$ are as defined above, n1+n2 is 3 to 7 with n2≥1.

11. The aqueous composition according to claim 1, wherein the at least one polyorganosiloxane A) has a number average molecular weight $M_n$ of less than 2000 g/mol, as determined by gel permeation chromatography (GPC) using polystyrene as standard.

12. The aqueous composition according to claim 1, wherein the surfactant is selected from the group consisting of cationic, nonionic, betaine and anionic surfactants.

13. The aqueous composition according to claim 1, wherein the surfactant has a HLB value ranging from 1 to 20.

14. The aqueous composition according to claim 1, wherein the surfactant is selected from hydrocarbon-based or silicone-based emulsifiers each being different from polyorganosiloxane A) and compound B).

15. The aqueous composition according to claim 1, wherein the surfactant is present in an amount of from about 0.05% to about 15% by weight of the aqueous composition.

16. The aqueous composition according to claim 1, comprising at least one additional additive, selected from the group consisting of
a) solvents,
b) proteins,
d) preservatives,
e) skin protecting ingredients,
g) oxidizing agents,
h) reducing agents,
i) tannins,
j) metal salts, and
k) further auxiliaries selected from the group consisting of pH adjusting agents, thickeners, lipids, amino acids, sugars, fragrances, sunscreen agents, vitamins, pearlescent agents, gelling agents, trace elements, sequestering agents, antioxidants, humectants, anti-hair loss agents, anti-dandruff agents, propellants, ceramides, polymers, fillers, nacres, colorants, and mixtures thereof,
with the proviso that oxidizing agents and reducing agents are not present simultaneously in a given composition.

17. The aqueous composition according to claim 1 having the composition:

| Ingredient | Weight-% |
| --- | --- |
| polyorganosiloxane A) and/or compound B) | 0.05 to 30 |
| hydrocarbon or silicone based surfactant | 0 to 15 |
| water | q.s. to add to 100% |
| diluents/solvents | 0 to 95 |
| protein, preferred keratin | 0 to 15 |
| emollients/fatty substance | 0 to 15 |
| preservatives | 0 to 5 |
| skin protecting ingredients | 0 to 15 |
| conditioning agents | 0 to 15 |
| oxidizing agents | 0 to 15 |
| reducing agents | 0 to 15 |
| tannins | 0 to 15 |
| metal salts | 0 to 15 |
| hair dyeing agent | 0 to 15 |
| further auxiliary agents | 0 to 15 | wherein the wt-percentages relate to the complete weight of the aqueous composition.

18. The aqueous composition according to claim 1, which comprises at least one compound B), wherein $R^2$ has 2 to 50 carbon atoms.

19. The aqueous composition according to claim 18, which comprises at least one compound B), wherein $R^2$ is selected from divalent to decavalent hydrocarbon radicals which have 2 to 30 carbon atoms, and may contain optionally one or more groups selected from
—O—, —NH—, —C(O)—, —C(S)—, tertiary amino groups

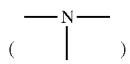

and quaternary ammonium groups

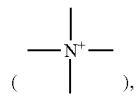

and wherein $R^2$ is substituted by one or more hydroxyl groups.

20. The aqueous composition according to claim 1, which comprises at least one hair dyeing agent present in an amount of from about 0.01 to about 5 wt. %.

21. The aqueous composition according to claim 1, which is selected from a hair shampoo composition, hair care composition, hair conditioning composition, hair strengthening composition, hair coloration or dyeing composition, hair combability improving composition, anti-frizz composition, hair rinse-off and leave-on compositions.

22. A hair treatment or hair care composition comprising one or more aqueous compositions according to claim 1.

23. A process for the treatment of hair which comprises the steps of providing an aqueous composition according to claim 1, and applying said aqueous composition to said hair.

24. The process of claim 23, further comprising the step of dyeing the hair.

25. A process for the treatment of hair according to claim 23 for strengthening of hair, for hair color retention, for hair color enhancement, for hair color protection, for shaping of hair, for hair conditioning, for hair smoothening or softening, for hair straightening, or for improving manageability of the hair.

26. An aqueous composition for hair treatment, comprising at least one organic compound B) selected from the formula:

$$R^2—(F)_{2-18}$$

wherein F is —O—C(O)—CH=CH—C(O)OH—, and $R^2$ is selected from hydrocarbon radicals having a valency of 2 to 18, which have up to 100 carbon atoms, and may optionally contain one or more groups selected from —O—, —NH—, —C(O)—, —C(S)—, tertiary amino groups

and quaternary ammonium groups

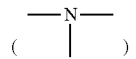

and wherein $R^2$ is substituted by one or more groups selected from hydroxyl groups and halogen atoms, and wherein the composition further comprises at least one surfactant, wherein the weight ratio of said surfactant to the polyorganosiloxane A) or the compound B) is from 0.06 to 5.

27. The aqueous composition of claim 26 further comprising at least one polyorganosiloxane A) having an average number of 2 to 1000 siloxy units selected from the siloxy groups of the formulas:

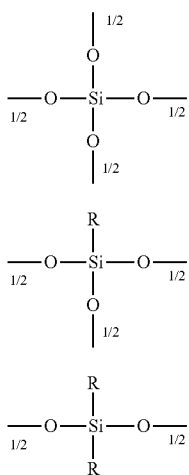

(Q)

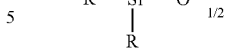

(T)

(D)

(M)

wherein each R is independently selected from $R^1$ and $R^F$, wherein $R^1$ is selected from organic groups bound to the silicon atoms by a carbon atom, and two groups $R^1$ may form a bridging group between two silicon atoms, and $R^F$ is selected from organic groups different from $R^1$ and is bound to the silicon atoms by a carbon atom, which contain at least one functional group F which is as defined with the proviso that the at least one polyorganosiloxane A) comprises at least one $R^F$ group.

* * * * *